United States Patent [19]
Yoshimura et al.

[11] Patent Number: 6,061,126
[45] Date of Patent: May 9, 2000

[54] DETECTING SYSTEM FOR SURFACE FORM OF OBJECT

[75] Inventors: Kazunari Yoshimura; Kuninori Nakamura; Yasuyuki Yuuki, all of Osaka, Japan

[73] Assignee: Matsushita Electric Works, Ltd., Osaka, Japan

[21] Appl. No.: 09/084,451

[22] Filed: May 27, 1998

[51] Int. Cl.$^7$ ............................................. G01N 21/00
[52] U.S. Cl. ........................ 356/237.1; 356/237.1; 356/237.2; 356/237.3; 356/237.4
[58] Field of Search ............................ 356/237.1, 237.2, 356/237.3, 237.4

[56] References Cited

U.S. PATENT DOCUMENTS 5,506,676  4/1996  Hendler et al. ...................... 356/237.1
5,715,050  2/1998  Haga ...................................... 356/237.1

*Primary Examiner*—Frank G. Font
*Assistant Examiner*—Reginald A. Ratliff
*Attorney, Agent, or Firm*—Sughrue, Mion, Zinn, Macpeak & Seas, PLLC

[57] ABSTRACT

A detecting system for a surface form of an object is disclosed. The system comprises a light source section emitting a plurality of slit-like probe rays incidenting on a predetermined inspected area of an inspected object at predetermined pitches, an image pick-up section imaging reflected lights of the probe rays from the inspected area, the image pick-up section imaging the reflected lights from a direction different from a transmission axis of the light source section, the image pick-up section disposed so as to image the reflected light from the inspected area in a batch, and a computation section converting image data from the image pick-up section into data of surface height of the inspected object using a trigonometrical survey method.

25 Claims, 28 Drawing Sheets

FIG.17
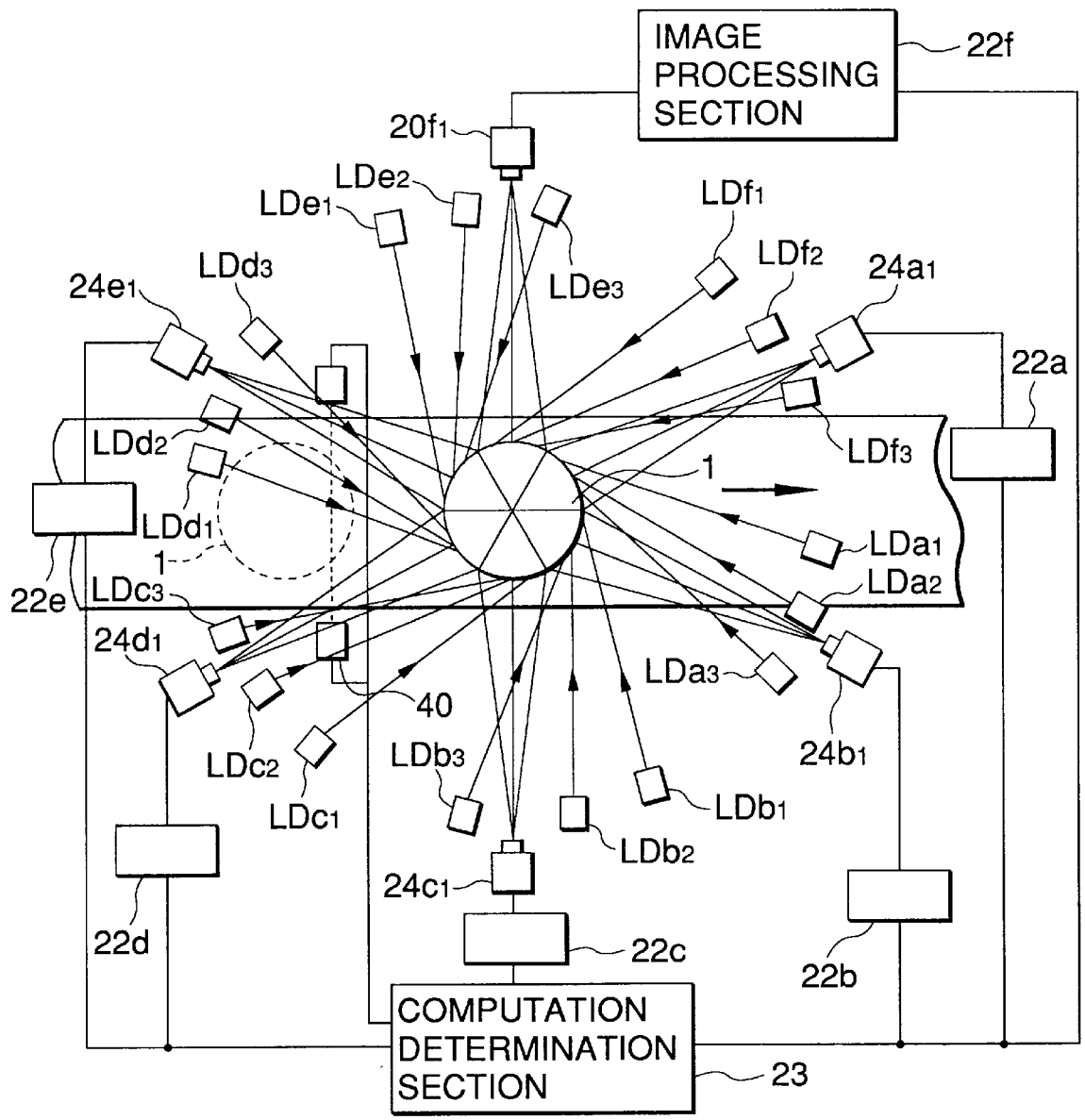
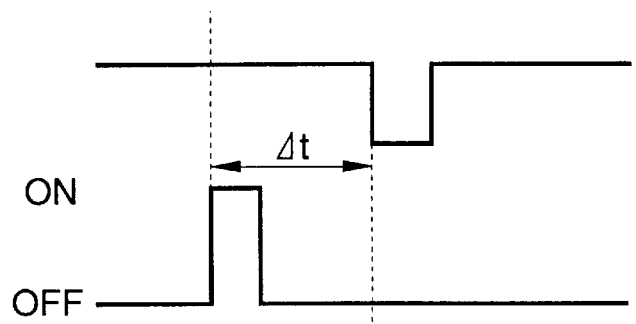
FIG.18(a)
FIG.18(b)

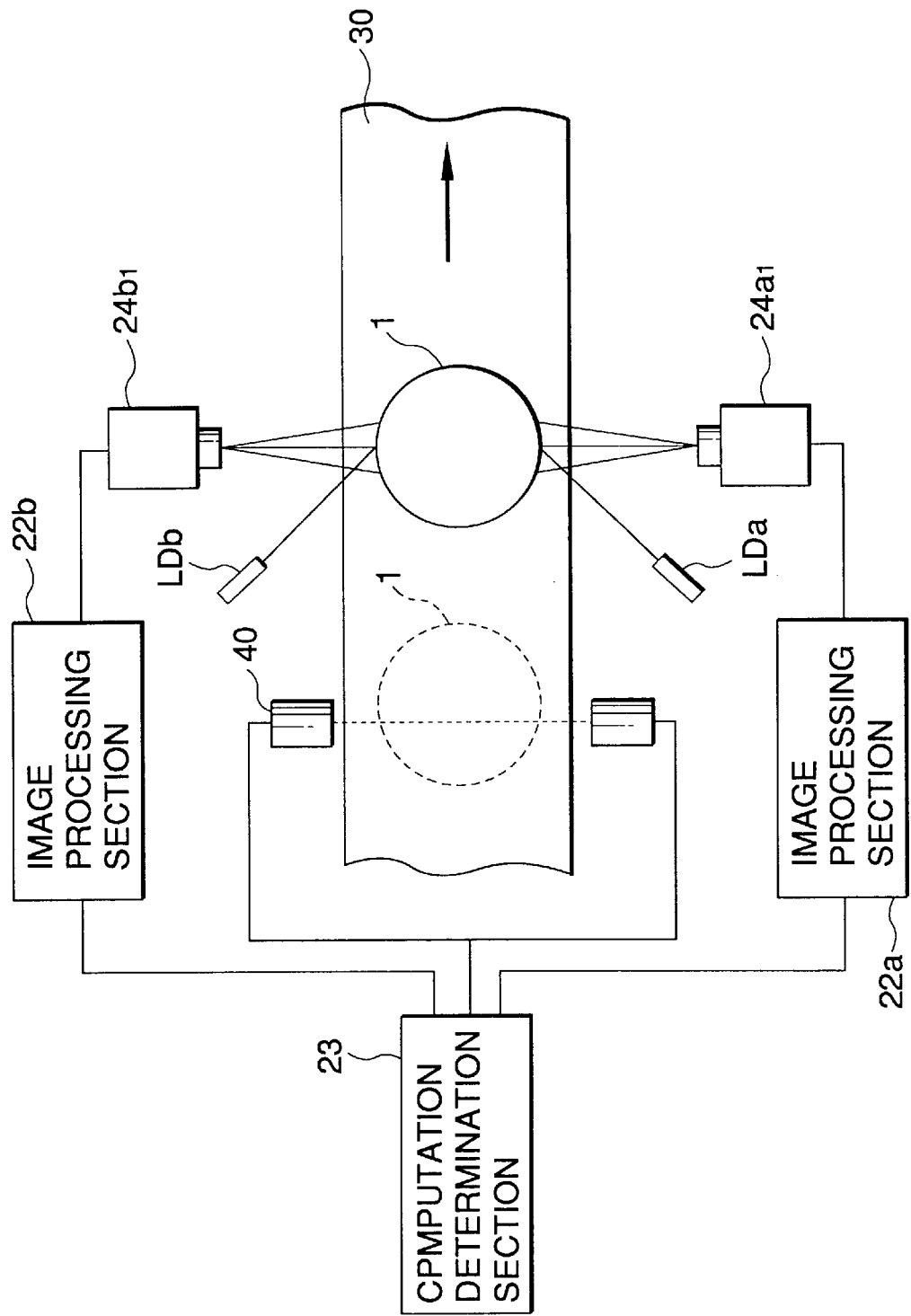

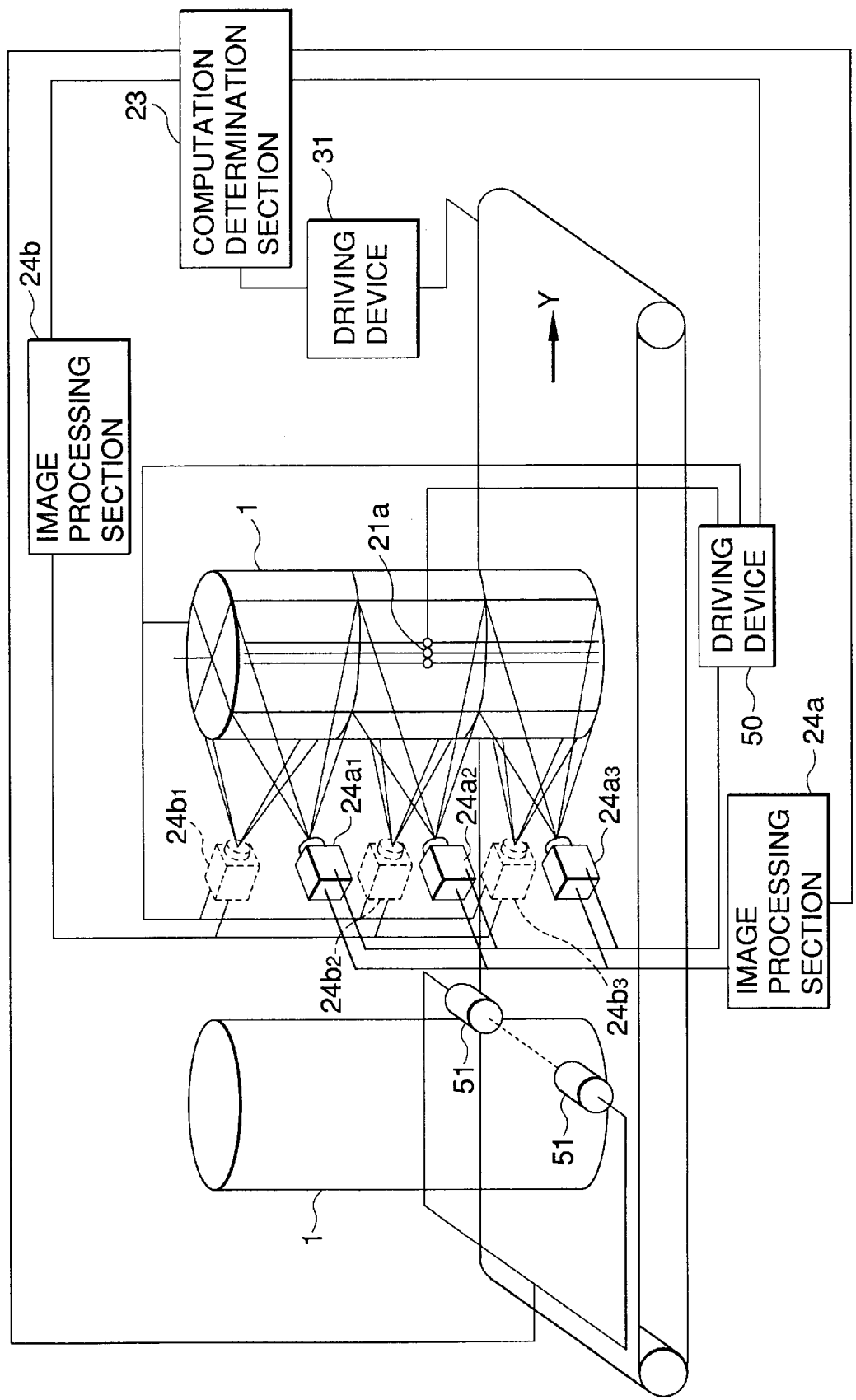

DETECTING SYSTEM FOR SURFACE FORM OF OBJECT

BACKGROUND OF THE INVENTION

1. Technical Field of the Invention

The present invention relates to a detecting system for detecting a surface flaw of a cylindrical object such as a can or a roll or a curved object such as a sphere by means of measuring an uneven form and height displacement of the object surface using a light-section method.

2. Background of the Related Art

FIG. 32 shows a conventional example (refer to the Unexamined Japanese Patent Publication No. Hei 6-167455). Here, one point of an inspected object 1 having a cylindrical appearance rotated and translated is irradiated with a light beam through a lens 3 from a light source 2, scattered light is imaged and detected by a detector 5 through a lens 4 from a different direction from a light transmission axis X of the light, and detection output of the detector 5 is input through an amplifier 6 to an A/D converter 7, which then converts the detection output from analog form into digital form. At the time, sampling is executed for a predetermined sampling rate by a timer 8. The converted data is sent to a microprocessor 11 via a store 9, which then makes a comparison between normal and defective faces, thereby detecting a defect, then displays the result on a display 12 and sends a control signal to a scrapping controller 13 for scrapping the inspected object 1.

By the way, in the conventional system, while a spot-like light beam is emitted, the inspected object 1 is rotated. Thus, desirable inspected area cannot be imaged at the same time and a dead zone (undetectable area) occurs between the spot beams. The two-step operation of rotating and translating the inspected object is required and the mechanism is complicated.

SUMMARY OF THE INVENTION

Therefore, a object of the present invention is providing an detecting system for surface form of object capable of imaging a predetermined inspection area (or a full periphery) at the same time without rotating an inspected object, thereby improving the speed and the accuracy of detecting the defect.

To accomplish the object, there is provided a detecting system for a surface form of an object which comprises a light source section emitting a plurality of slit-like probe rays incidenting on a predetermined inspected area of an inspected object at predetermined pitches, an image pick-up section imaging reflected lights of the probe rays from the inspected area, the image pick-up section imaging the reflected lights from a direction different from a transmission axis of the light source section, the image pick-up section disposed so as to image the reflected light from the inspected area in a batch, and a computation section converting image data from the image pick-up section into data of surface height of the inspected object using a trigonometrical survey method.

To detect the defect on the surface of a cylindrical object, there is provided a detecting system which comprises at least one light source section emitting a plurality of slit-like probe rays incidenting on predetermined inspected area of a cylindrical inspected object at predetermined pitches, at least one image pick-up section imaging reflected lights of the probe rays from the corresponding inspected area, each image pick-up section detecting the reflected lights from a direction different from a transmission axis of the corresponding light source section, each image pick-up section disposed so as to image the reflected lights from the corresponding inspected area in a batch, and a computation section converting image data from the image pick-up sections into data of surface height of the inspected object using a trigonometrical survey method, wherein total inspected area defined by the light source section and the image pick-up section covers full periphery of surface of the cylindrical inspected object.

In this manner, the defect can be detected at high speed with high accuracy without rotating the inspected object.

According to the present invention, each of the probe rays may incident at the same angle with the tangents at incidence points on the inspected object.

In this manner, the measurement can always be executed at constant resolution and high accuracy can be provided.

According to the present invention, the detecting system may further comprise a first inspection position wherein the light source section and the image pick-up section are disposed so as to pick-up the image of a half periphery surface of the cylindrical inspected object, a second inspection position wherein the light source section and the image pick-up section are disposed so as to pick-up the image of remained half periphery surface of the cylindrical inspected object, and a transporter transporting the inspected object to the first inspection position, and transporting to the second inspection position after the first image pick-up.

In this manner, the inspected object can be inspected on the full periphery without being rotated on the same transporter.

According to the present invention, the transporter may further include a rotation mechanism rotating the cylindrical inspected object at predetermined angle after the first image pick-up to set the inspected area for the second image pick-up.

In this manner, the number of image pick-up devices and that of slit light sources can be decreased.

According to the present invention, the detecting system may further comprise a passing detection sensor provided upstream of the inspection position and detecting the passing of the inspected object, wherein the image pick-up is started after predetermined period from the passing detection of the inspected object.

In this manner, the defect can be detected with high accuracy.

According to the present invention, the image pick-up section may include a plurality of image pick-up devices disposed at equal pitches in the vertical direction, each of the image pick-up devices images respective inspected area defined so as to equally divide all surface of the inspected object.

In this manner, the defect can be detected with high accuracy.

According to the present invention, the light source section may include a light source and a light divergence member providing the plurality of slit probe rays from the light source.

In this manner, the number of light sources can be decreased.

According to the present invention, the image pick-up section may include a plurality of image pick-up devices disposed so that a blind spot does not occur in the inspected area.

In this manner, the defect can be detected with high accuracy.

According to the present invention, the detecting system may be constructed so that the slit probe rays does not cross at right angle to plane defined by the transmission axis of the light source section and sight line axis of the image pick-up section.

In this manner, since stray light from the light source is prevented from being incident on the image pick-up device, a defect can be detected with high accuracy.

According to the present invention, the slit light rays may be emitted as many as the number for previously compensating a position shift in a direction orthogonal to the transport direction of the inspected object.

In this manner, if a position shift occurs, the measurement is less affected.

According to the present invention, the light source section may be single light source emitting intermittently single probe ray at predetermined time interval at which the inspected object moves as long as long distance as the pitch of the slit probe rays within the time from the image pick-up start to end.

In this manner, the number of light sources can be decreased.

According to the present invention, the light source section and the image pick-up section may be disposed so as not to contact the moving inspected object during the image pick-up.

In this manner, the image pick-up section and the light source section cannot interfere with the inspected object moving on the transporter and the defect can be detected with high accuracy.

According to the present invention, the detecting system may further comprise a distance measuring sensor detecting a position shift amount of the inspected object in a direction orthogonal to the transport direction of the inspected object, and a correction member correcting the positions of the light source section and the image pick-up position based on position shift data from the distance measuring sensor.

In this manner, the defect can be detected with high accuracy.

BRIEF DESCRIPTION OF THE DRAWINGS

In the accompanying drawings:

FIG. 17 is a plan layout drawing of the main part of the system of the seventh embodiment of the present invention;

FIG. 18 is a time chart to describe the operation of the system of the seventh embodiment of the present invention;

FIG. 20 is a plan layout drawing of the main part of the system of the eighth embodiment of the present invention;

FIG. 22 is a perspective view of a system of a ninth embodiment of the present invention;

DETAILED DESCRIPTION OF THE PREFERRED EMBODIMENTS

Figure 1:
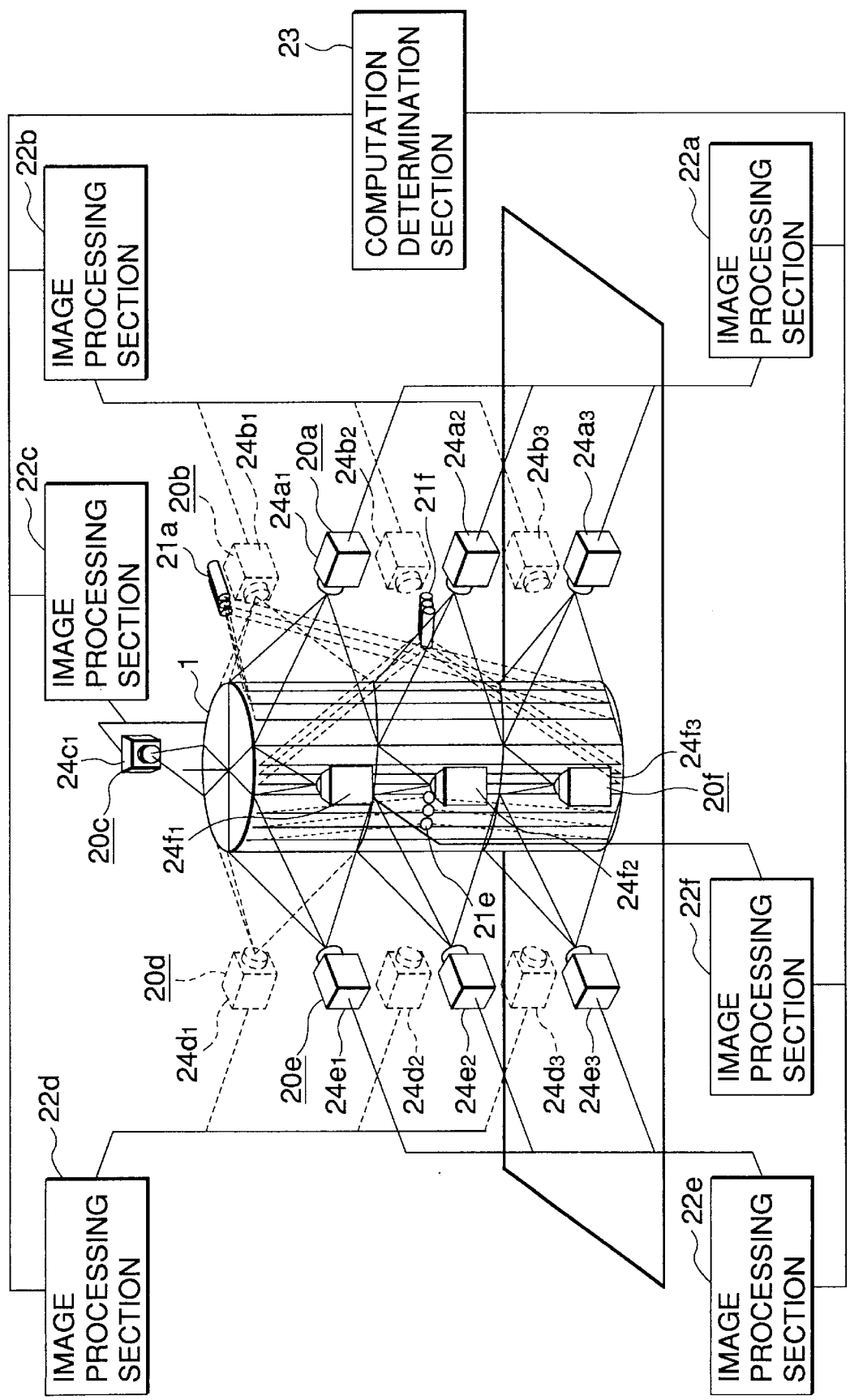
FIG. 1 is a perspective view of a system of a first embodiment of the present invention.

Preferred embodiments of the present invention will be discussed below in detail.

1. First Embodiment

In a first embodiment, an inspected object 1 having a cylindrical appearance is surrounded by image pick-up sections 20a . . . for imaging reflected light from the surface of the inspected object 1 and light source groups 21a . . . for transmitting slit light rays as light section lines, placed at predetermined intervals in the circumferential direction (for example, at equal intervals by assuming that the angle viewed from the center of the inspected object 1 is 60 degrees), and image processing sections 22a . . . for processing image pick-up signals provided by the image pick-up sections 20a . . . and a computation determination section 23 for converting image pick-up data provided by the image processing sections 22a . . . into height data are included.

Figure 2:
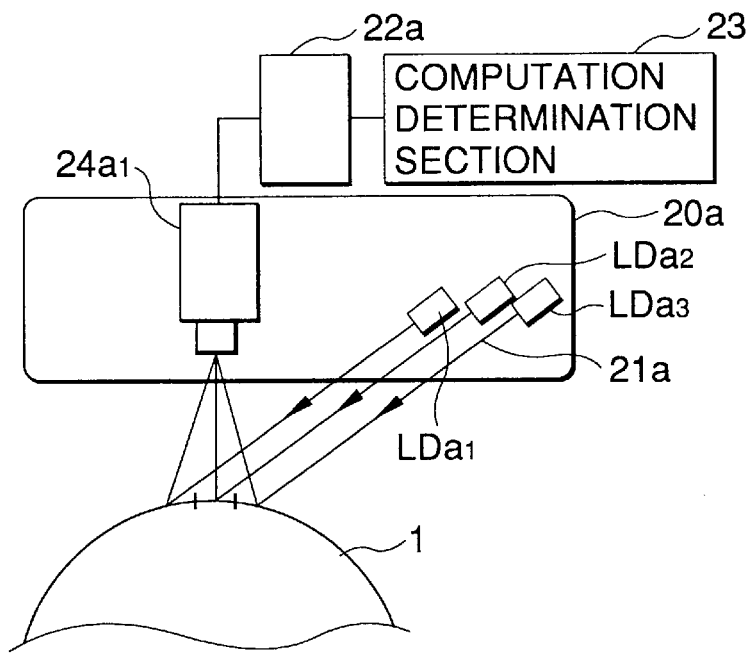
FIG. 2 is a schematic representation of the system of the first embodiment of the present invention.

Each light source group 21a . . . consists of three light sources LDa1 to LDa3, . . . , as shown in FIG. 2, and slit light rays transmitted from the light sources LDa1 to LDa3, . . . are parallel to each other and are incident on the inspected object 1 at predetermined pitches. The reflected light of the slit light rays emitted from the light sources LDa1 to LDa3, . . . of the light source group 21a . . . is imaged by the image pick-up section 20a . . . placed in the inspection area corresponding to the light source group 21a. . . .

In the embodiment, each image pick-up section 20a . . . is made up of three image pick-up devices 24a1–24a3 . . . placed at predetermined intervals along the axis of the inspected object 1 so as to correspond to, for example, an upper inspection area, an intermediate inspection area, and a lower inspection area set within the incidence range of slit light rays from the corresponding light source group 21a. . . . Image pick-up signals (image signals) of the three image pick-up devices 24a1–24a3 . . . are sent to the image processing section 22a . . . corresponding to the image pick-up section 20a. . . .

Each image pick-up section 20a . . . and the light source group 21a . . . corresponding thereto make up an image pick-up unit. In FIG. 1, the light source groups corresponding to the image pick-up sections 20b–20d are not shown.

Figure 3:
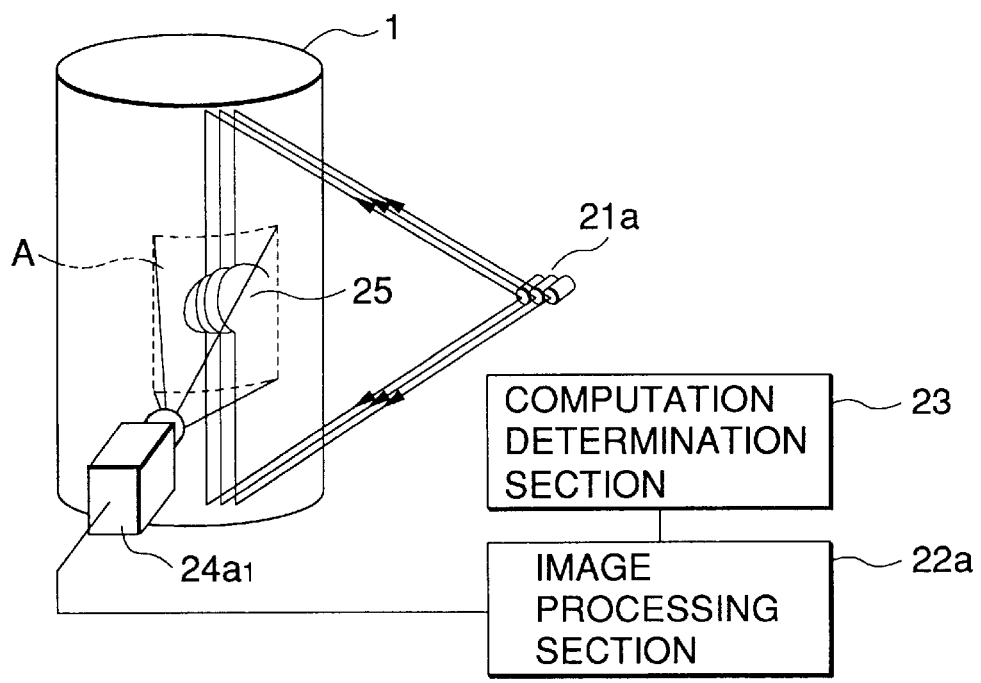
FIG. 3 is a schematic representation to show the operation of the system of the first embodiment of the present invention.

When the surface of the inspected object 1 is irradiated with slit light rays made of laser light emitted from the light sources LDa1–LDa3, . . . of the light source groups 21a . . . , if the surface of the inspected object 1 like a cylinder contains a defect 25 as shown in FIG. 3, the linear slit light rays are detected as lines curved due to the dent of the defect 25. The computation determination section 23 finds a shift amount from the straight line as the number of pixels based on the data image provided by the image processing section 22a . . . and then calculates the depth of the dent of the defect 25 from angle θ between the transmission light axis of the slit light and the tangent at the incidence point.

Figure 31:
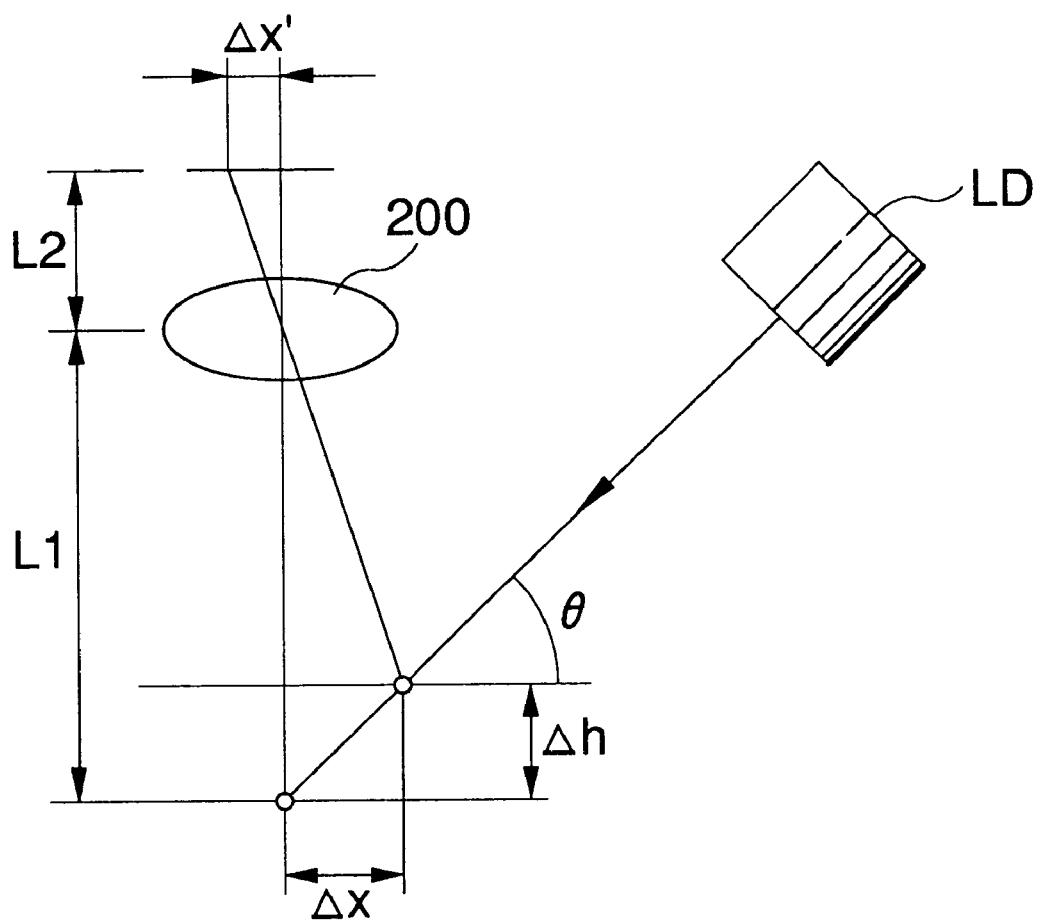
FIG. 31 is a schematic representation of the principle of a trigonometrical survey used with the present invention.
Figure 32:
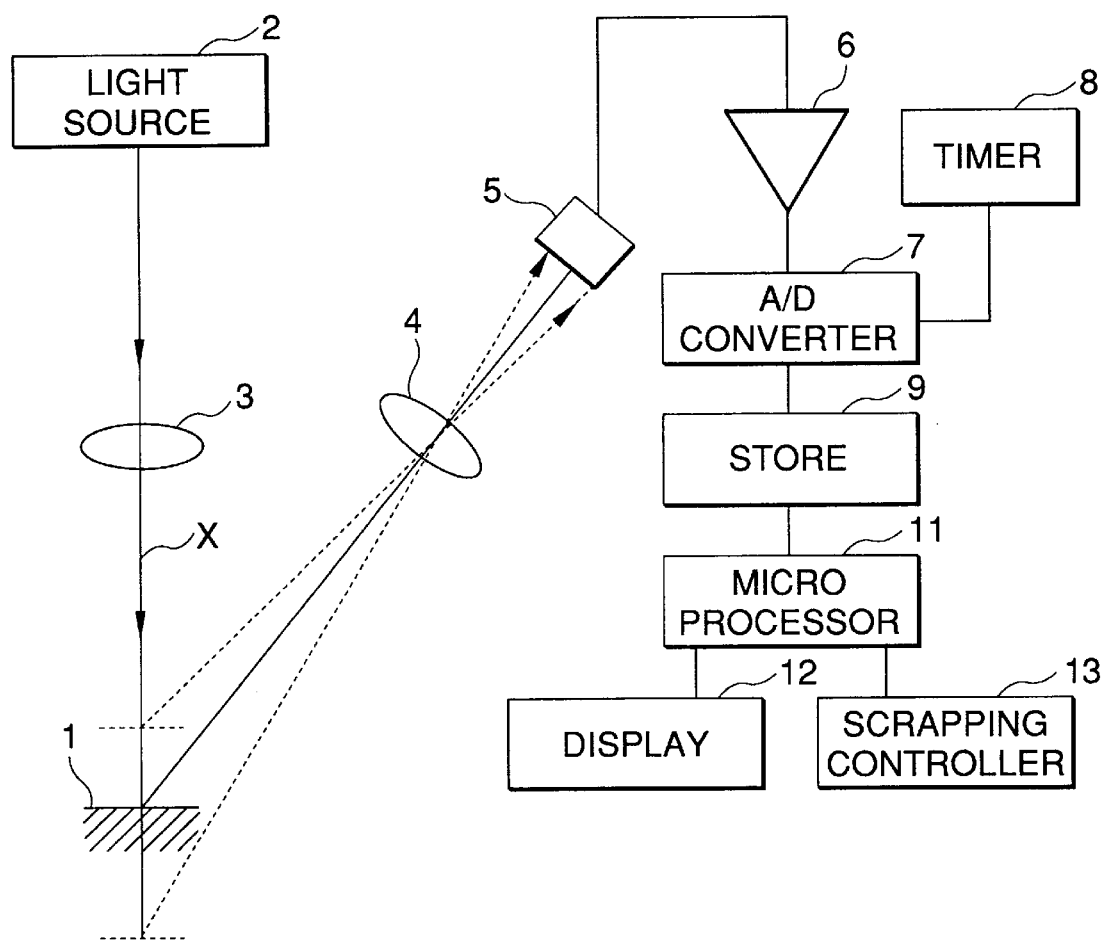
FIG. 32 is a block diagram of a conventional system.

The principle of finding the depth of the defect 25 by making a trigonometrical survey will be discussed based on a principle illustration of FIG. 31.

First, assuming that height displacement is Δh when the distance between the surface of the inspected object 1 and a lens 200 of an image pick-up section 20 is L1 and the distance between the lens 200 and an image pick-up device (not shown) is L2, the height displacement Δh is represented as Δx and Δh/Δx=tanθ.

When the displacement amount on the image pick-up device is Δx', the relation $$\Delta x'/\Delta x = L2/L1$$

is used to represent the height displacement Δh on the image pick-up device as follows:

$$\Delta x' = (L2/L1) \cdot (1/\tan\theta) \cdot \Delta h$$

where Δx' denotes image data and Δh denotes height data (depth data).

Therefore, the image processing section 22a . . . stores the image data (Δx') read by the image pick-up device of the image pick-up section 20a . . . in memory in the image processing section and finds height data image Δh. On the other hand, the computation determination section 23 compares height amount Δh' obtained from the data image processed by the image processing section 22a . . . with a standard value. If the height amount Δh' exceeds the standard value, the computation determination section 23 determines the inspected object to be defective and outputs the determination result (in this case, NG). LD denotes a light source.

At this time, reflected light from the inspected object 1 in inspection area A determined by the field of view of each image pick-up device 24a1–24a3, . . . of each image pick-up section 20a . . . placed surrounding the inspected object 1 is imaged in batch, thus eliminating the need for rotating the inspected object 1 so that all the area can be detected between the image pick-up start and end.

In the embodiment, the number of slit light rays in one inspection area A is three, but if the number of slit light rays is increased for narrowing the pitches, a finer defect 25 can be detected, needless to say.

In the embodiment, each image pick-up section 20a . . . is made up of three image pick-up devices 24a1–24a3, but the number of image pick-up devices making up one image pick-up section is not limited to three depending on, for example, the field of imaging view of the image pick-up device. The intervals at which the image pick-up sections 20a . . . are as well.

2. Second Embodiment

Figure 4:
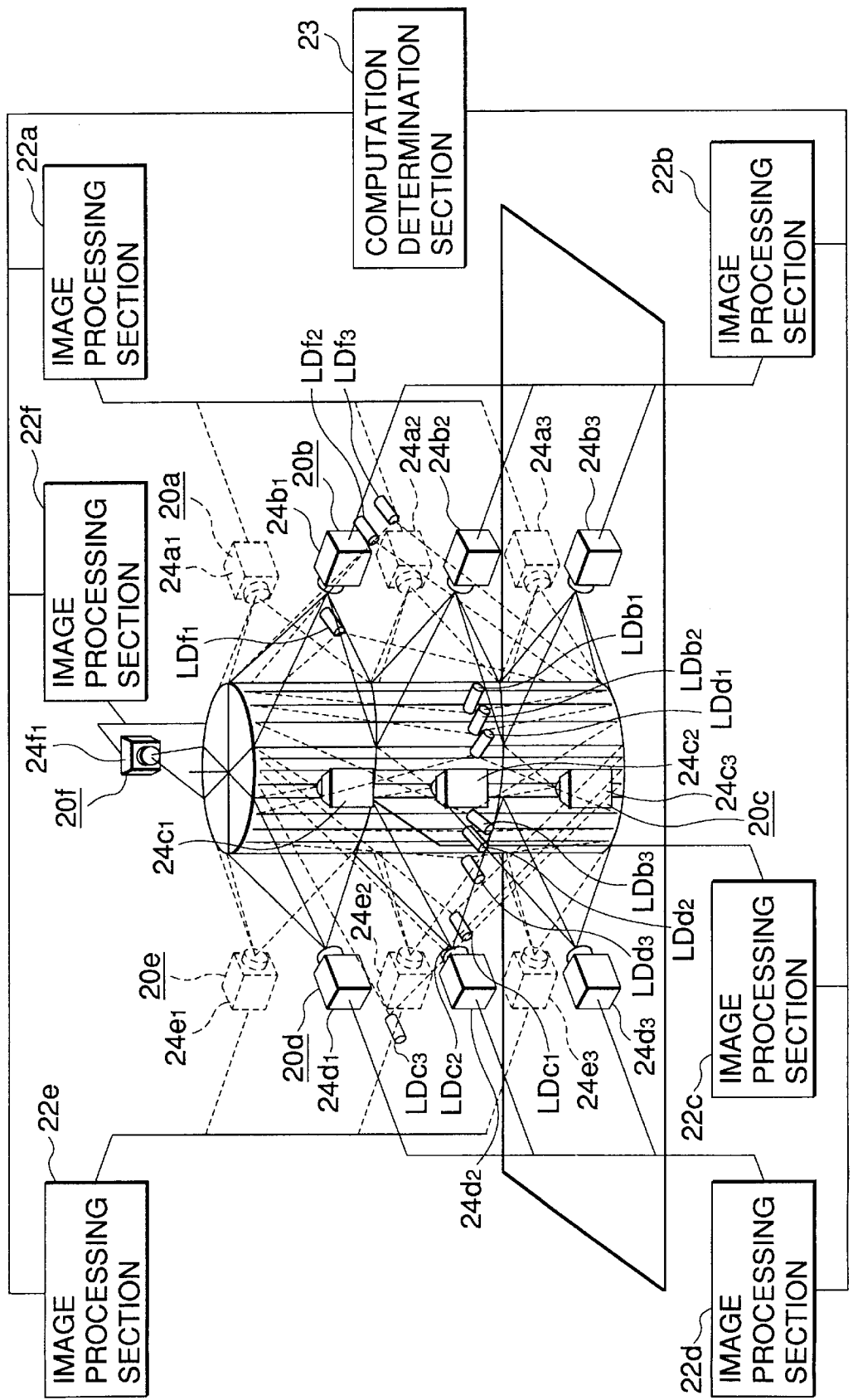
FIG. 4 is a perspective view of a system of a second embodiment of the present invention.

As shown in FIG. 4, an inspected object 1 having a cylindrical appearance is surrounded by image pick-up sections 20a . . . for imaging reflected light from the surface of the inspected object 1 and light source groups 21a . . . for transmitting slit light rays as light section lines, placed at predetermined intervals in the circumferential direction (for example, at equal intervals), and image processing sections 22a . . . for processing image pick-up signals provided by the image pick-up sections 20a . . . and a computation unit 23 for converting image pick-up data provided by the image processing sections 22a . . . into height data are included, as well in the first embodiment. The second embodiment differs from the first embodiment in placement of light sources LDa1–LDa3, . . . making up each light source group 21a. . . .

Figure 5:
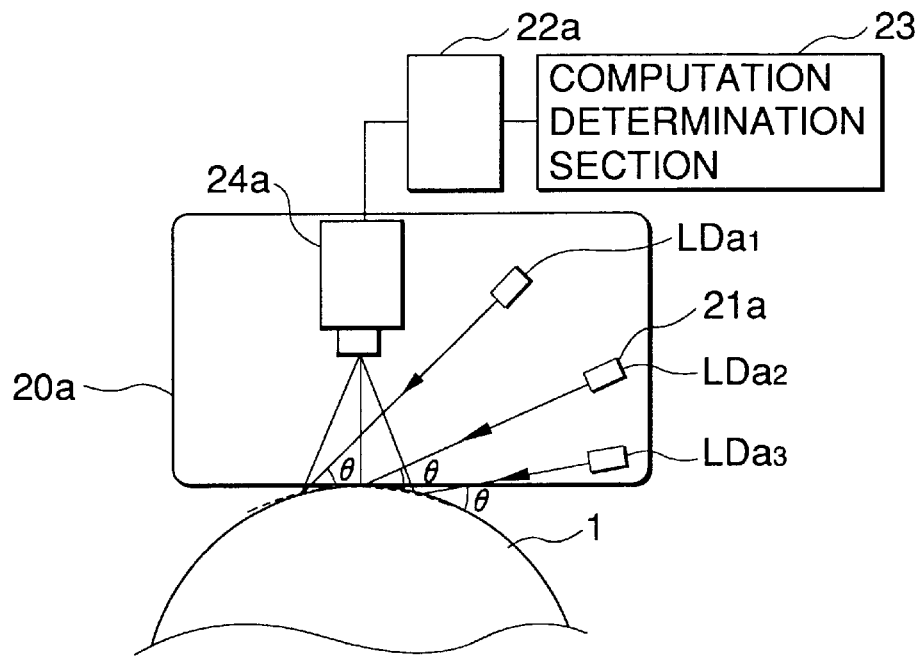
FIG. 5 is a schematic representation of the system of the second embodiment of the present invention.
Figure 6:
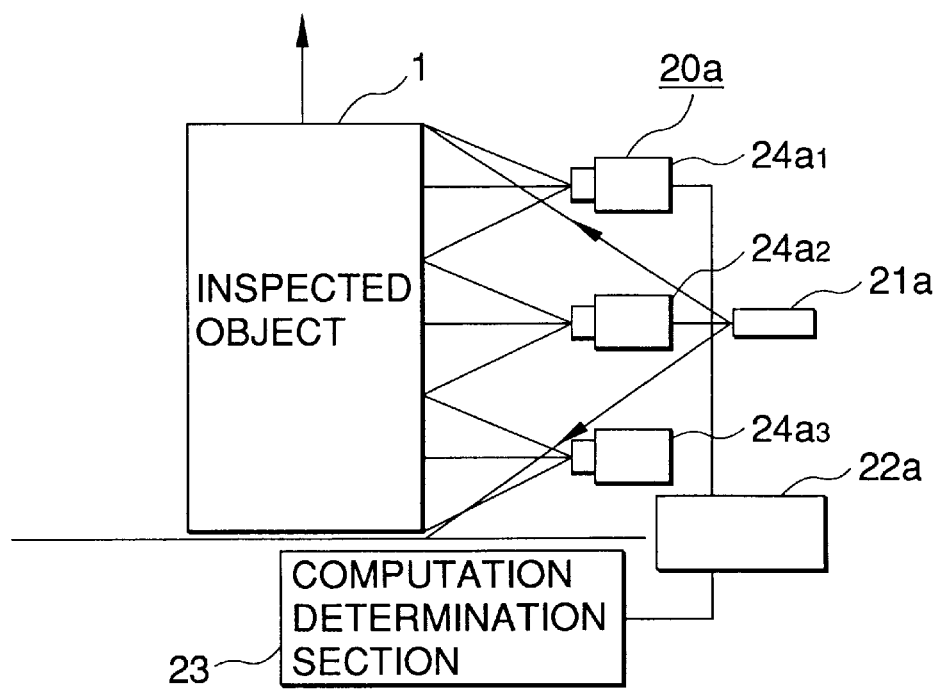
FIG. 6 is a plan layout drawing of the main part of the system of the second embodiment of the present invention.
Figure 7:
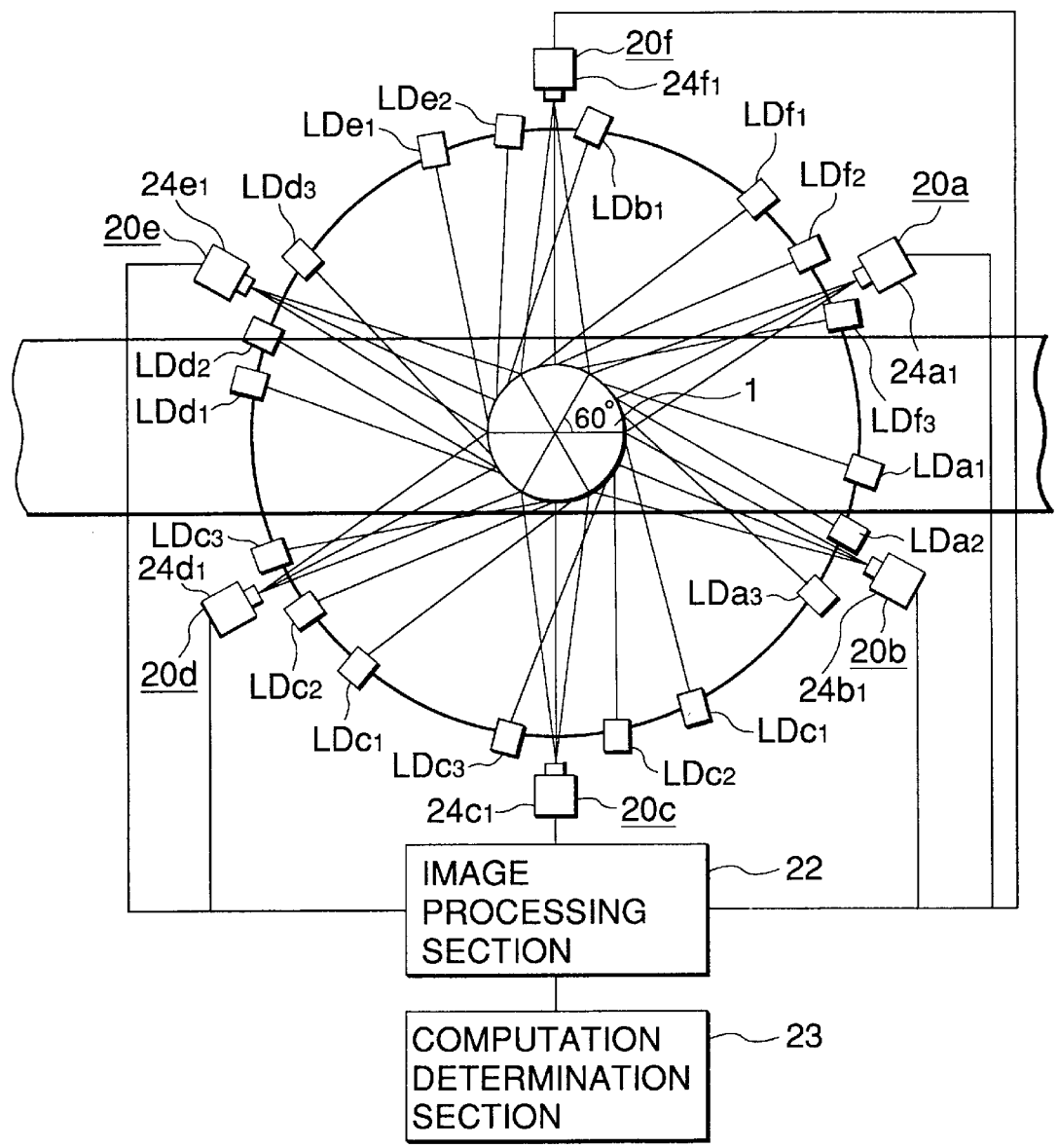
FIG. 7 is a side layout drawing of the main part of the system of the second embodiment of the present invention.

That is, as shown in FIG. 5 to FIG. 7, the light sources $LDa_1$–$LDa_3$, . . . are placed so that slit rays emitted from the light sources $LDa_1$–$LDa_3$, . . . are always incident at the same angle θ with the tangents at the incidence positions on the surface of the inspected object 1 like a cylinder and are incident on the inspected object 1 at predetermined pitches. In FIG. 4, the light sources $LDa_1$–$LDa_3$, . . . are placed so that the slit light rays are incident at about 30 degrees with the tangents, and all incidence angles of the slit light rays from the light sources $LDa_1$–$LDa_3$, . . . are equal. Thus, equal resolution can be provided at any position. In FIG. 7, only one image processing section 22 is provided for the image pick-up sections 20a–20f, but image processing sections 22 may be provided in a one-to-one correspondence with the image pick-up sections 20a–20f.

As in the first embodiment, reflected light from the inspected object 1 in one inspection area A is detected in batch, thus eliminating the need for rotating the inspected object 1 so that all the area can be detected between the image pick-up start and end. To detect a fine defect 25, the number of slit light rays may be increased, as in the first embodiment.

Also in the second embodiment, each image pick-up section 20a . . . is made up of three image pick-up devices $24a_1$–$24a_3$, but the number of image pick-up devices making up one image pick-up section is not limited to three depending on, for example, the field of imaging view of the image pick-up device. The intervals at which the image pick-up sections 20a . . . are as well.

3. Third Embodiment

Figure 8:
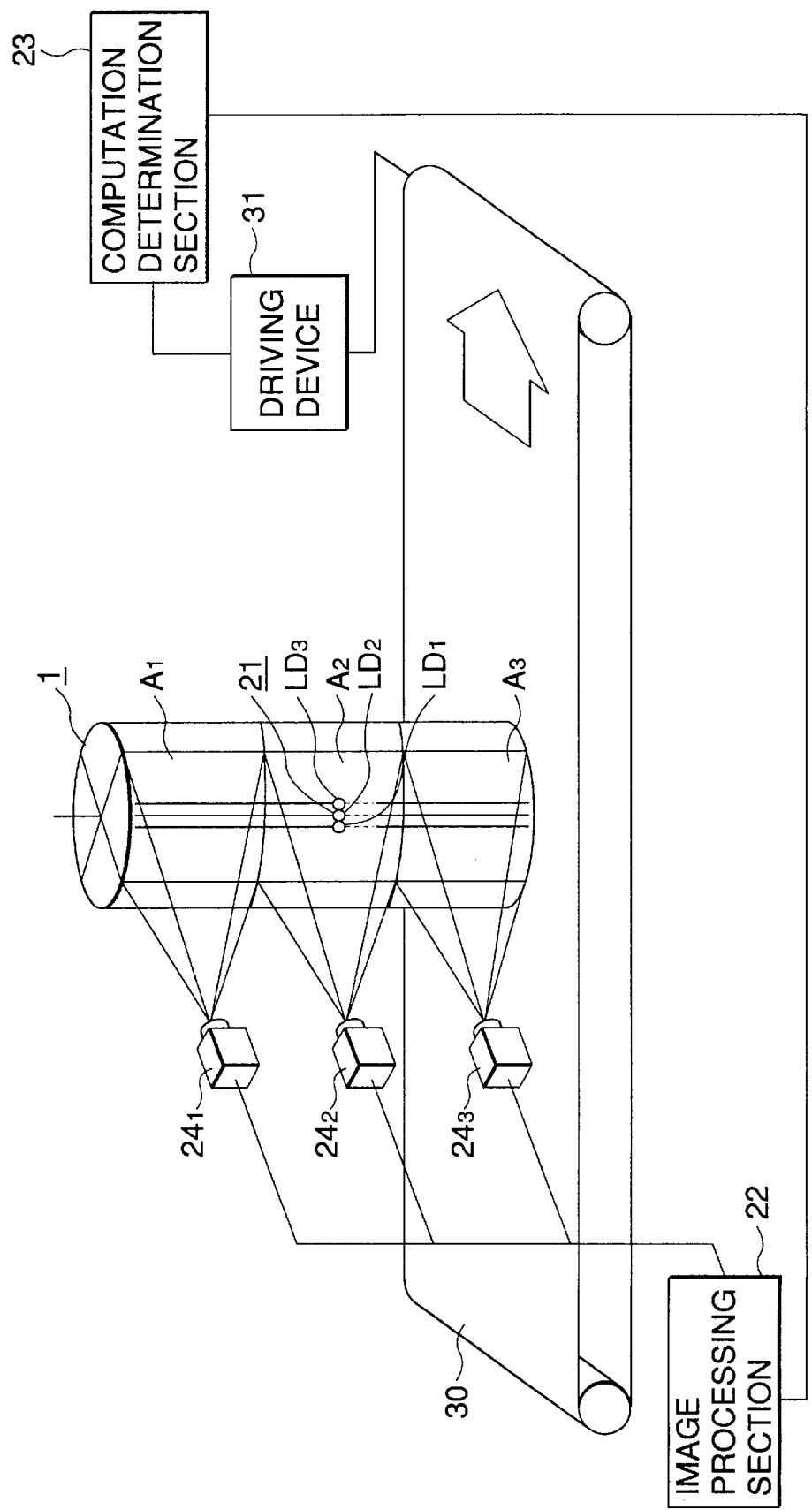
FIG. 8 is a perspective view of a system of a third embodiment of the present invention.
Figure 9:
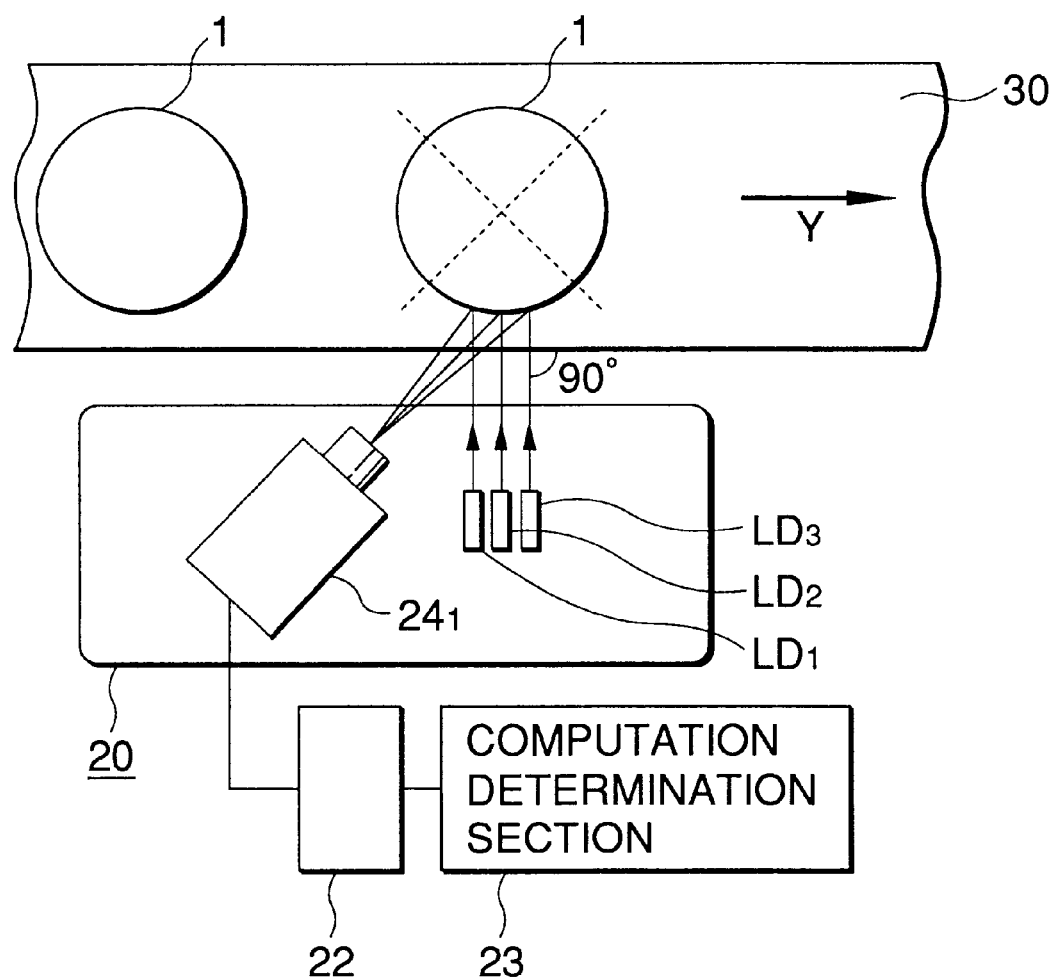
FIG. 9 is a plan layout drawing of the main part of the system of the third embodiment of the present invention.

As shown in FIG. 8 and FIG. 9, there are placed three light sources $LD_1$–$LD_3$ of a light source group 21 for allowing parallel slit light rays to be incident on the surface of an inspected object 1 moving on a transporter 30 like a belt conveyor at right angles to moving direction Y of the inspected object 1, and three image pick-up devices $24_1$–$24_3$ of an image pick-up section 20 are placed in a direction different from the slit light incidence direction for imaging reflected light from the inspected object 1 in inspection area A1 . . . determined by the field of view of each image pick-up device $24_1$–$24_3$ in batch. Numeral 31 in FIG. 8 is a driving device of the transporter 30 and the driving device 31 is controlled by a computation unit 23.

4. Fourth Embodiment

Figure 10:
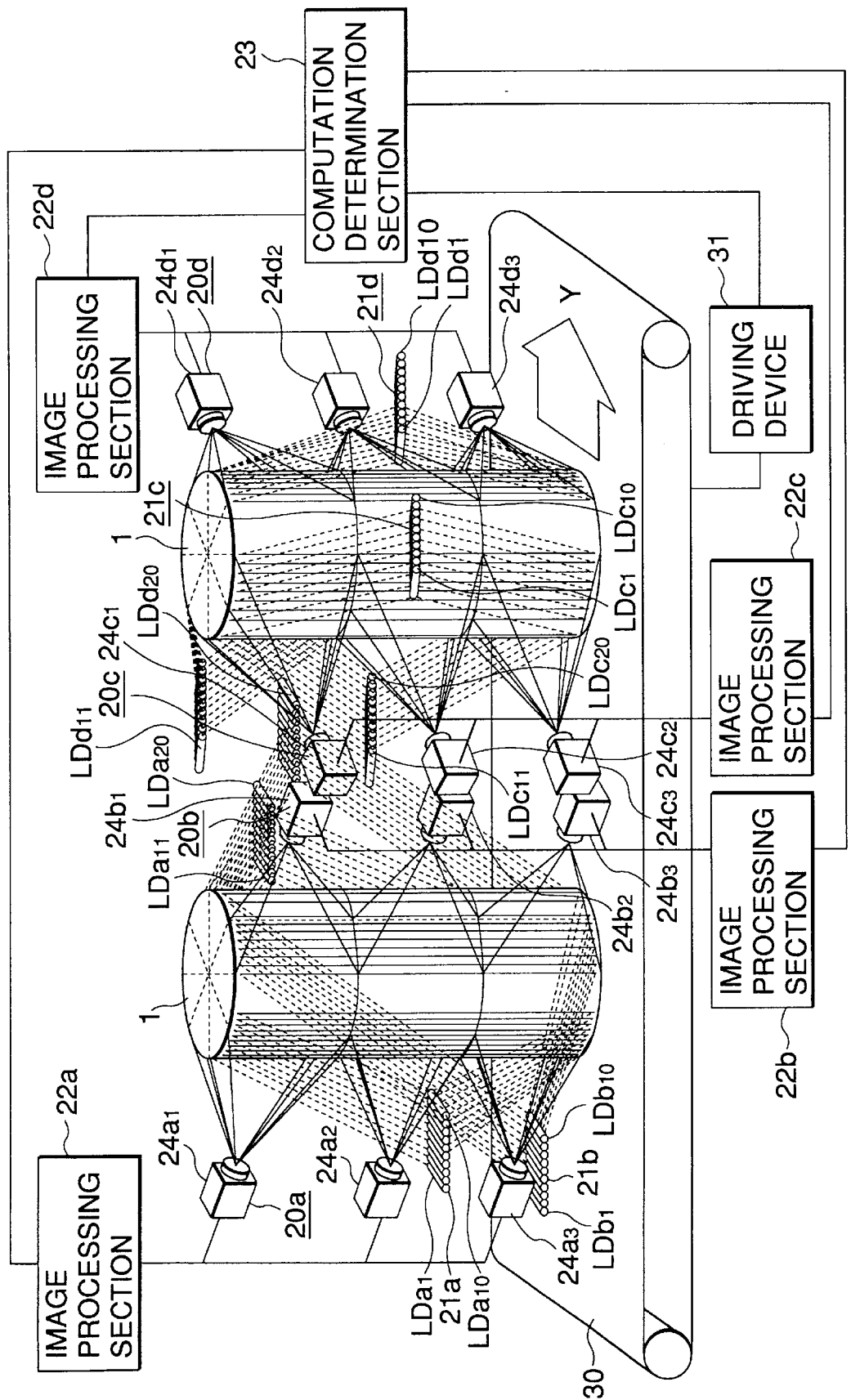
FIG. 10 is a perspective view of a system of a fourth embodiment of the present invention.
Figure 11:
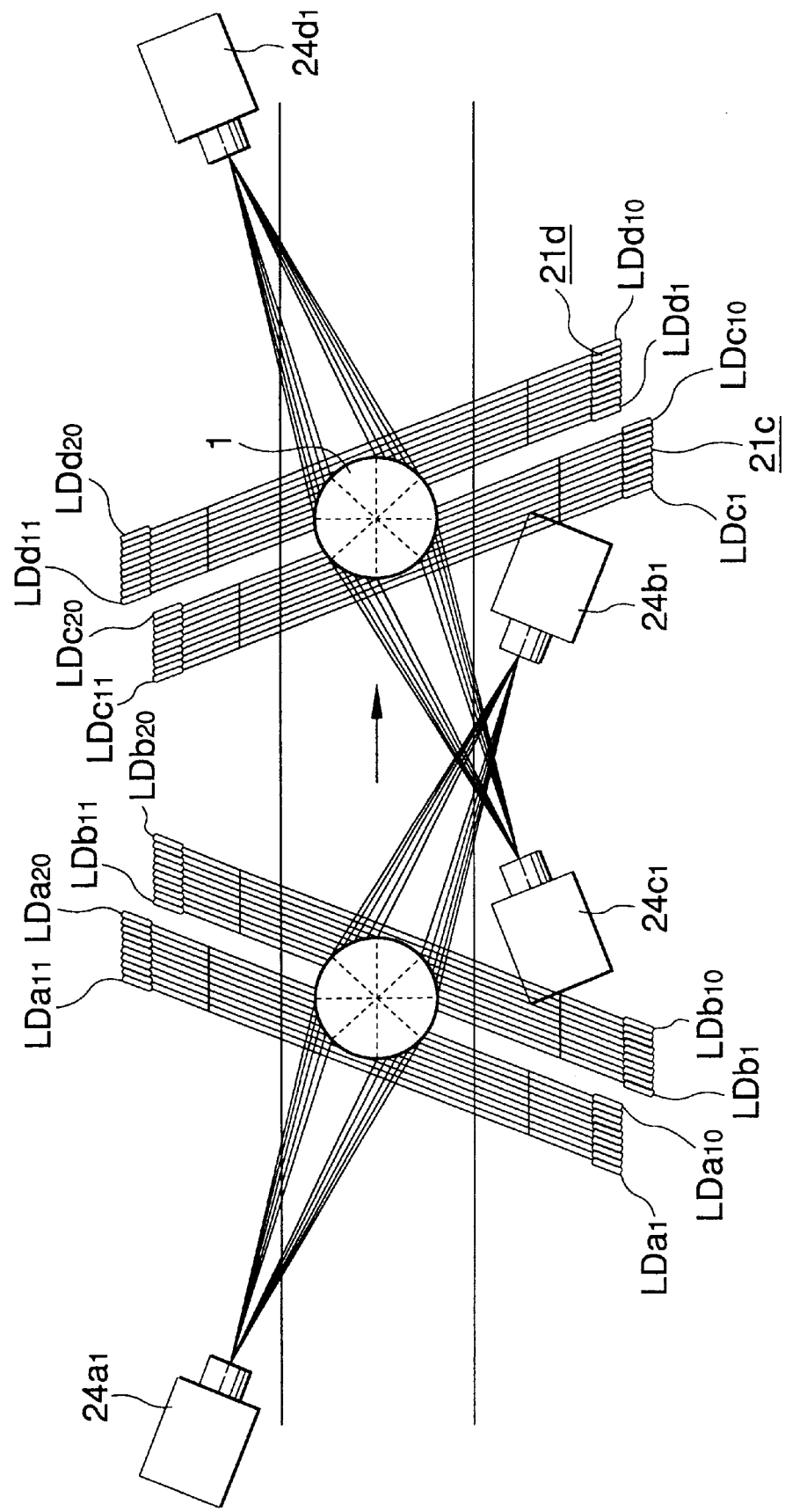
FIG. 11 is a plan layout drawing of the main part of the system of the fourth embodiment of the present invention.

As shown in FIG. 10 and FIG. 11, an optical system comprises four image pick-up units each consisting of a light source group 21a . . . for applying slit light rays, an image pick-up section 20a . . . , and an image processing section 24a . . . , wherein the image pick-up units are paired and the paired units face each other and are inclined at a predetermined angle with moving direction Y of an inspected object 1 moving on a transporter 30 so as to sandwich the inspected object 1 therebetween.

The light source group 24a . . . of each image pick-up unit emits as many slit light rays as the number for previously compensating a shift of the inspected object (light sources of the light source group corresponding to each image pick-up section, such as $LDa_{11}$–$LDa_{20}$ consisting of $LDa_1$–$LDa_{10}$ for the image pick-up section 20a or $LDb_{11}$–$LDb_{20}$ consisting of $LDb_1$–$LDb_{10}$ for the image pick-up section 20b). For example, even if the inspected object 1 shifts in the orthogonal direction with respect to the moving direction of the inspected object 1, if the light is projected wider than the width of the inspected object 1, the shift effect lessens. Each image pick-up device $24a_1$–$24a_3$, . . . of each image pick-up section 20a . . . picks up an image so as to be able to detect only a predetermined area of the surface of the inspected object 1. After the image pick-up sections 20a and 20b perform the first imaging and measurement, the inspected object 1 is moved to a predetermined position and the image pick-up sections 20c and 20d image and measure the inspection area contiguous to the first area. Thus, the inspected object 1 can be inspected on the full periphery while it is transported without being rotated.

5. Fifth Embodiment

Figure 12:
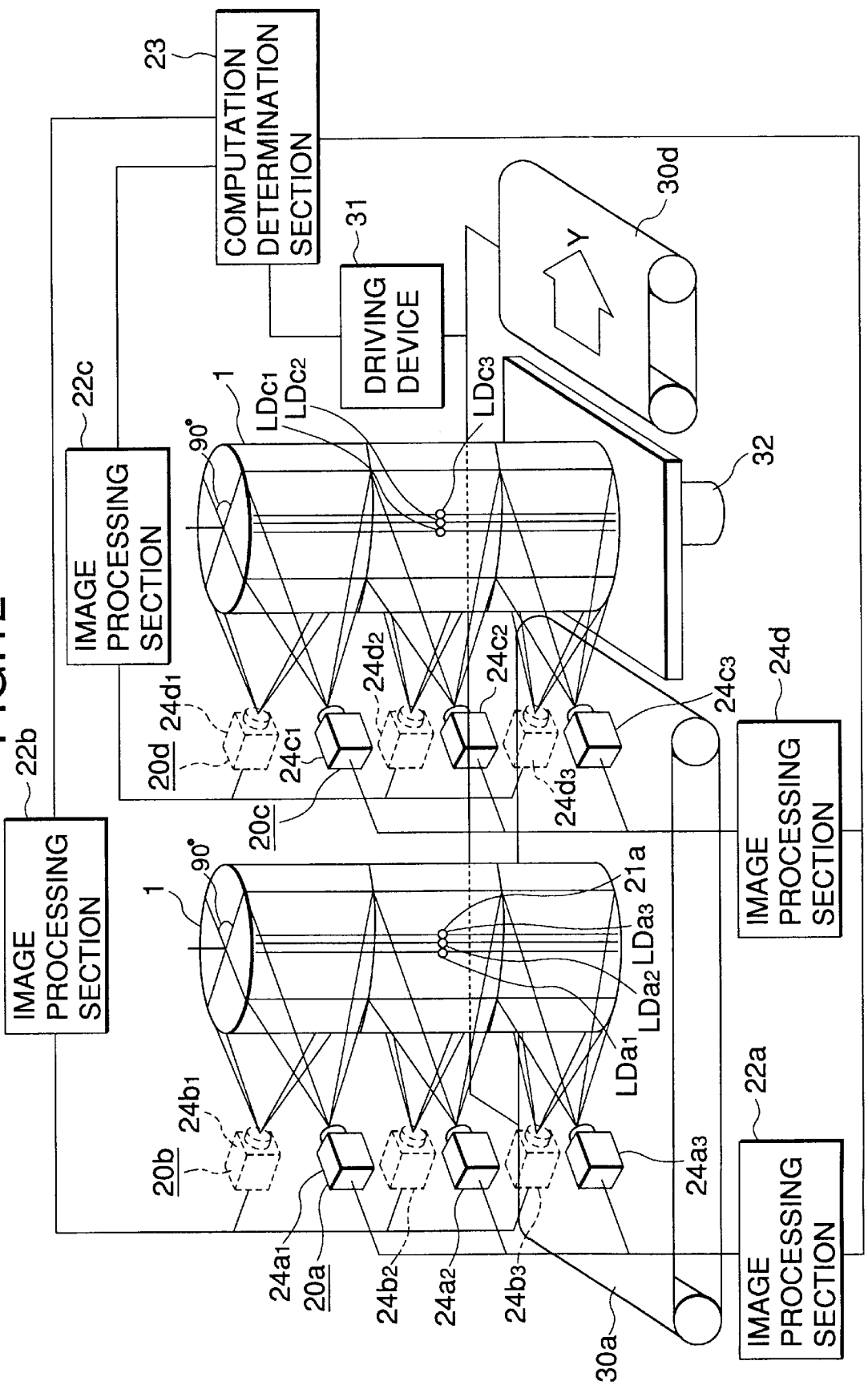
FIG. 12 is a perspective view of a system of a fifth embodiment of the present invention.
Figure 13:
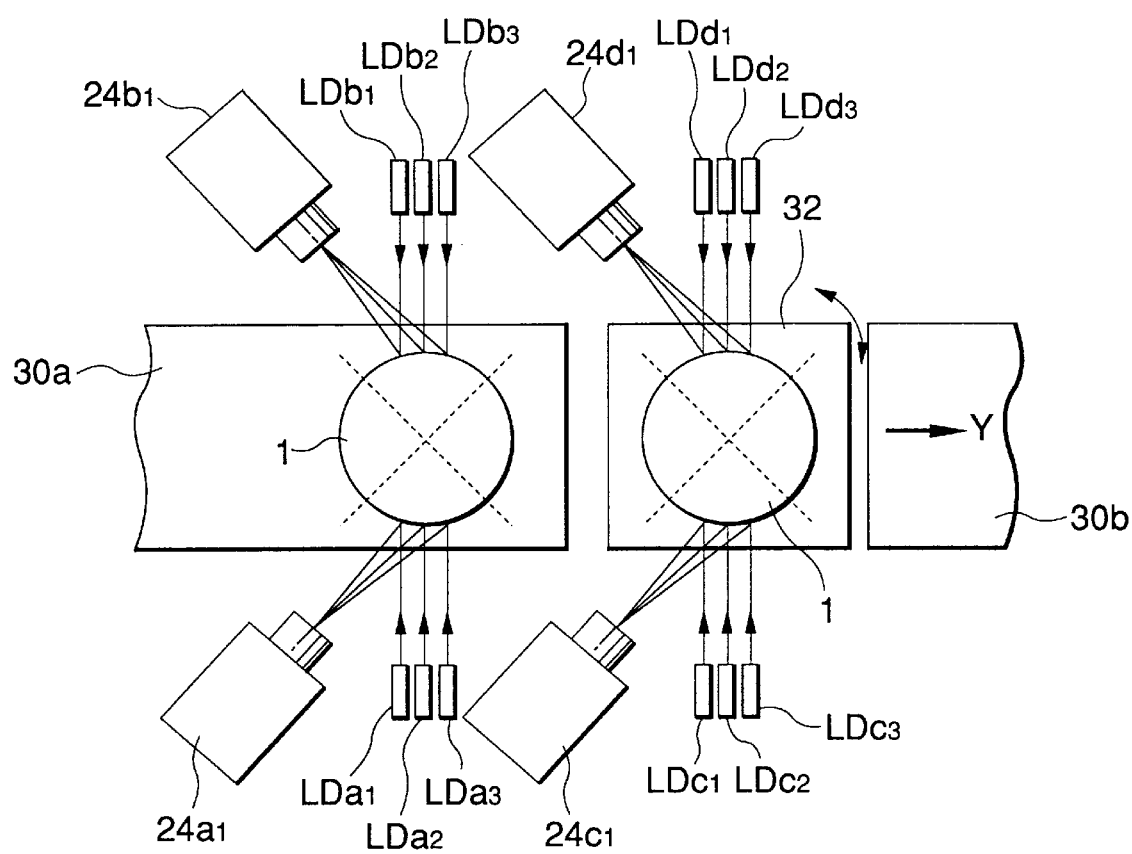
FIG. 13 is a plan layout drawing of the main part of the system of the fifth embodiment of the present invention.

As shown in FIG. 12 and FIG. 13, in an optical system, a rotating device 32 for horizontally rotating an inspected object 1 placed thereon is placed between transporters 30a and 30b. On the side of the transporter 30a, two light source groups 21a and 21b for projecting slit light rays on the surface of the moving inspected object 1 are placed at right angles to the moving direction of the inspected object 1 on both sides of the transporter 30a so as to face each other with the inspected object 1 therebetween. Each image pick-up device $24a_1$–$24a_3$, $24b_1$–$24b_3$ of an image pick-up section 20a, 20b corresponding to each light source group 21a, 21b images only a predetermined inspection area of the surface of the inspected object 1.

Likewise, at the position of the rotating device 32, two light source groups 21c and 21d for projecting slit light rays on the surface of the moving inspected object 1 are placed at right angles to the moving direction of the inspected object 1 on both sides of the rotating device 32 so as to face each other with the inspected object 1 therebetween. Each image pick-up device $24c_1$–$24c_3$, $24d_1$–$24d_3$ of an image pick-up section 20c, 20d corresponding to each light source group 21c, 21d images only a predetermined inspection area of the surface of the inspected object 1.

After the image pick-up sections 20a and 20b perform the first imaging and measurement at the position of the transporter 30, the inspected object 1 is rotated by a predetermined angle by the rotating device 32 for setting the next inspection area in the image pick-up position of the image pick-up sections 20c and 20d, which then perform the second imaging and measurement.

6. Sixth Embodiment

Figure 14:
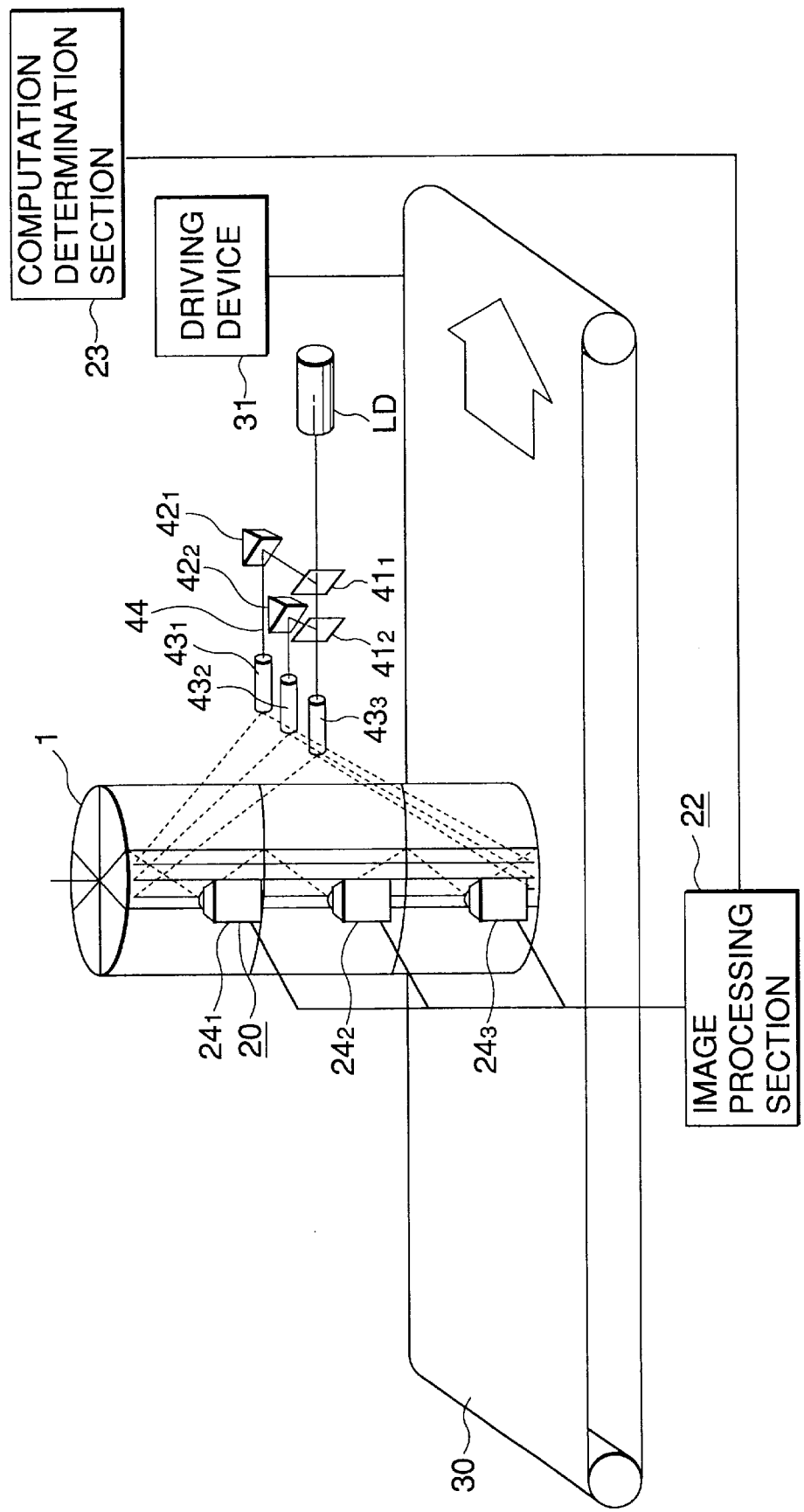
FIG. 14 is a perspective view of a system of a sixth embodiment of the present invention.
Figure 15:
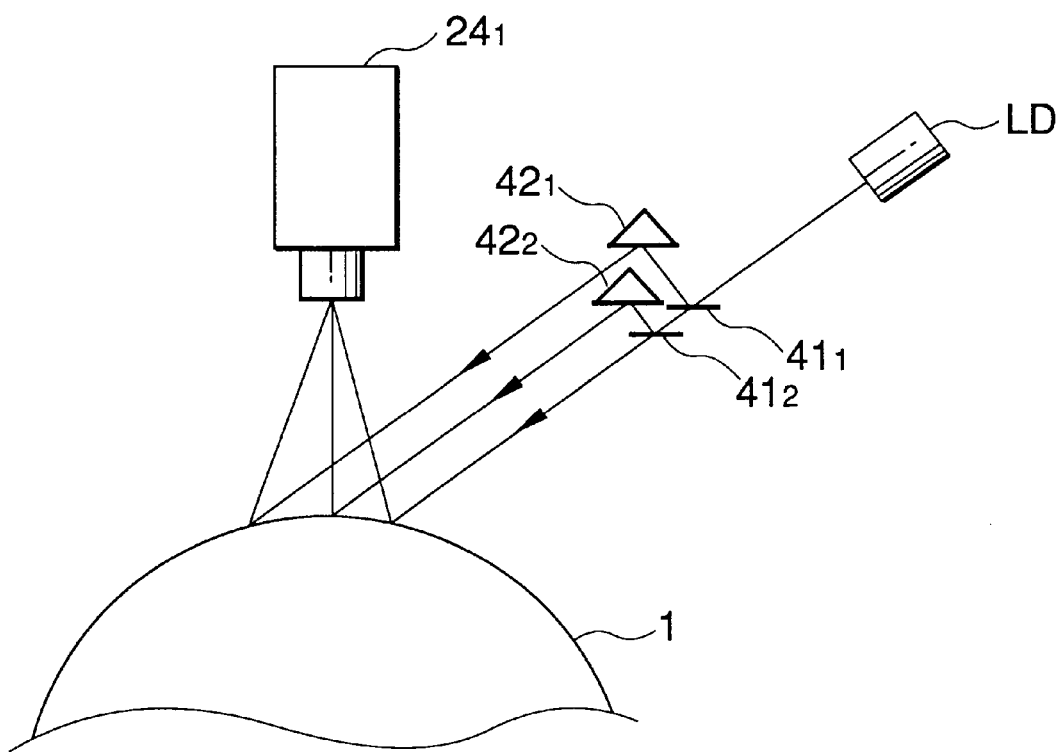
FIG. 15 is a schematic representation of the system of the sixth embodiment of the present invention.

As shown in FIG. 14 and FIG. 15, slit light generated from a single light source LD is made to diverge to a predetermined number of light rays by light divergence section 44 consisting of a half mirror $41_1$ . . . , a total reflection mirror $42_1$ . . . , and a cylindrical lens $43_1$ . . . , disposed on a light path to provide slit light rays. The slit light rays are incident on an inspected object 1 in parallel.

In the embodiment, one image pick-up section 20 consisting of image pick-up devices $24_1$–$24_3$ is installed. To include more than one image pick-up section, light source sections each made up of a light source LD and light divergence sections are provided in a one-to-one correspondence with the image pick-up sections 20, needless to say.

According to the method of the embodiment, the number of light sources can be decreased.

7. Seventh Embodiment

Figure 16:
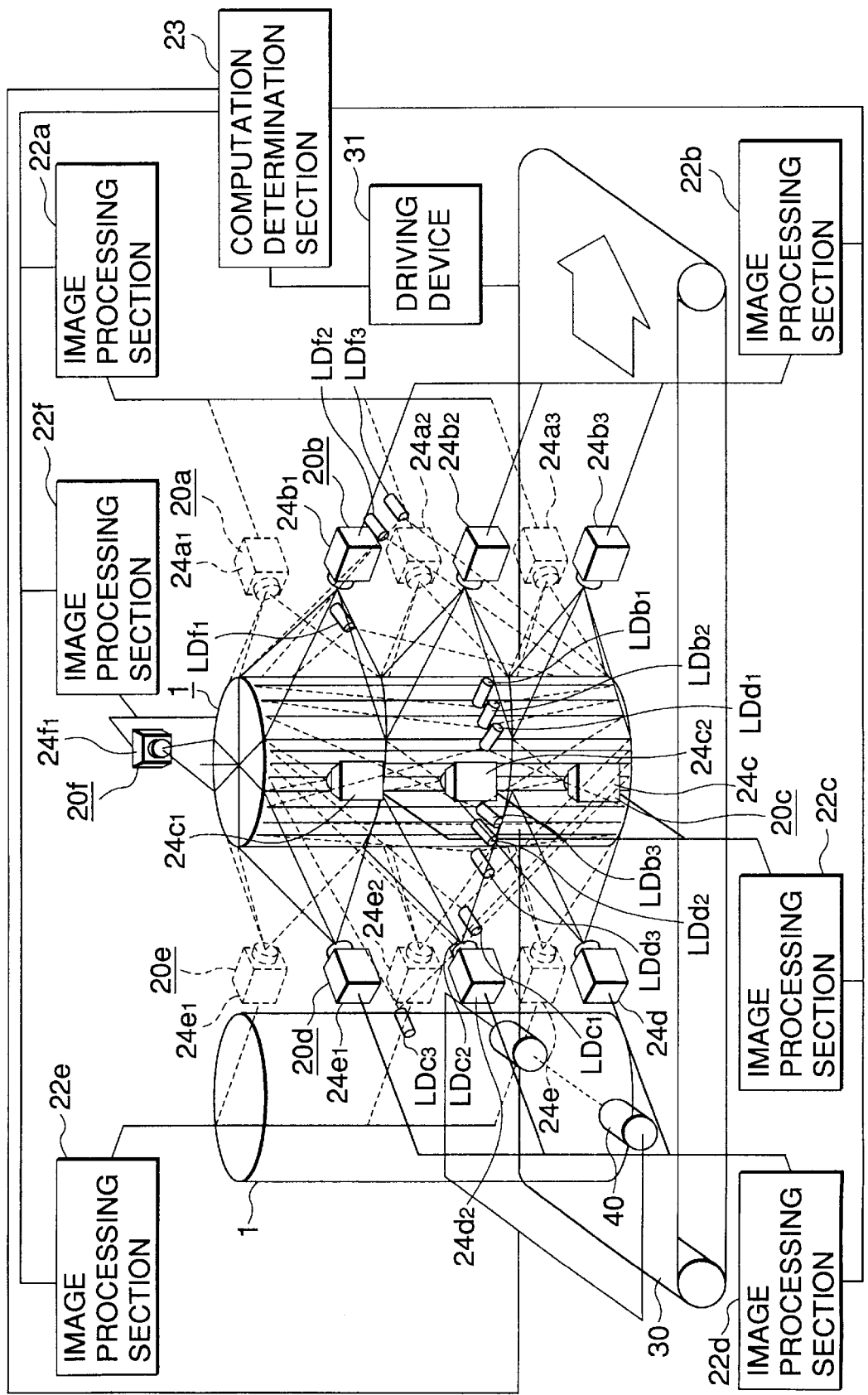
FIG. 16 is a perspective view of a system of a seventh embodiment of the present invention.

When inspected objects 1 flow intermittently on the transporter 30 as described above, they are often transported at unequal pitches. In such a case, if the inspected objects 1 are repeatedly imaged at equal pitches, no inspected object 1 may exist at the regular image pick-up position. As shown in FIG. 16 and FIG. 17, a shading photoelectric sensor 40 for sensing an inspected object 1 is installed on a transporter 30. If imaging is started after the expiration of predetermined time $\Delta t$ as shown in FIG. 18a with a detection signal of the photoelectric sensor 40 shown in FIG. 18b as a trigger after the instant at which an inspected object 1 crosses the photoelectric sensor 40 is sensed, whenever an inspected object 1 exists at a constant image pick-up position, it can be imaged and the image of the inspected object 1 can be obtained even if the transport pitches are irregular.

Image pick-up sections 20a . . . and light source groups 21a . . . corresponding thereto are placed as in shown in FIG. 4. Members identical with those previously described with reference to FIG. 4 are denoted by the same reference numerals in FIG. 16 and will not be discussed again.

8. Eighth Embodiment

Figure 19:
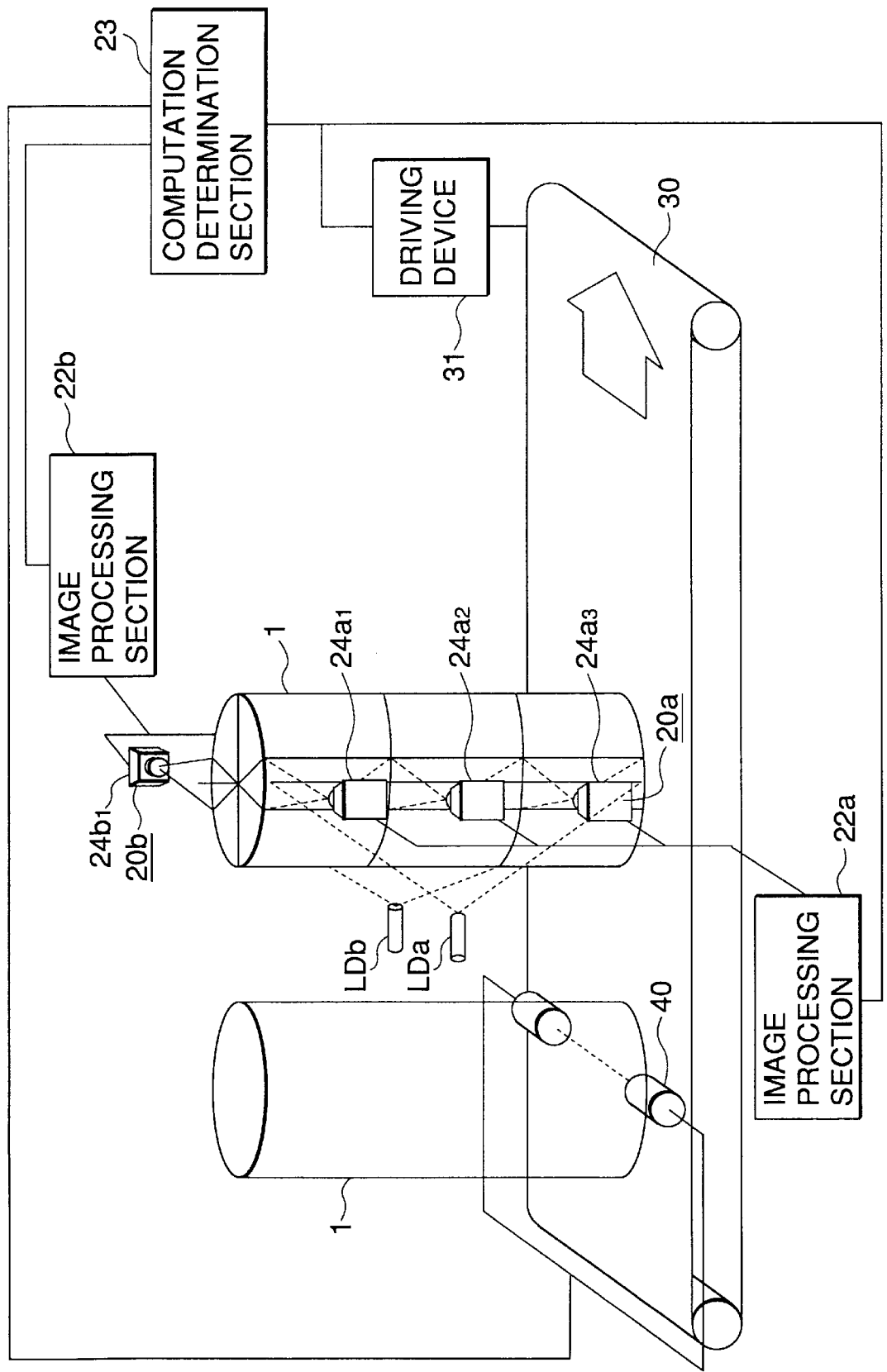
FIG. 19 is a perspective view of a system of an eighth embodiment of the present invention.
Figure 21A:
FIG. 21 is a time chart to describe the operation of the system of the eighth embodiment of the present invention.
Figure 21B:
Figure 21C:
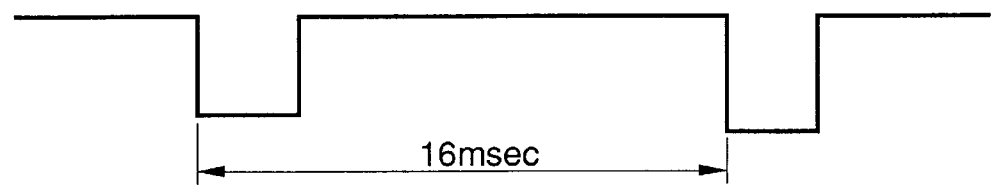

An inspected object 1 on a transporter 30 shown in FIG. 19 and FIG. 20 is moved at high speed. Two image pick-up sections 20a and 20b are placed on both sides of the transporter 30 so as to be at right angles to the moving direction of the inspected object 1 and face each other with the inspected object 1 between. Single light sources for applying slit light rays corresponding to the image pick-up sections 20a and 20b are provided therein in a one-to-one correspondence with the image pick-up sections 20a and 20b. Light source LDa, LDb is operated intermittently more than once as shown in FIG. 21b for applying slit light rays at the time interval at which the inspected object 1 moves as long distance as the slit light pitch within the image pick-up time of each image pick-up device $24a_1$–$24a_3$, $24b_1$–$24b_3$, namely, the time of 16 msec shown in FIG. 21c from the image pick-up start to end in a constant time after a detection signal of the inspected object 1 is output from a photoelectric sensor 40 as shown in FIG. 21a.

That is, the light sources LDa and LDb are placed so that one slit light ray projected on the field of view of image pick-up element of a CCD camera forming each image pick-up device 24a . . . corresponds to one horizontal scanning line of the image pick-up element and the inspected object 1 is irradiated with light instantaneously. If the inspected object 1 is irradiated with light once more within the time when one horizontal scanning line is output in accordance with a horizontal synchronizing signal, it is imaged as reflected light of the slit light of the light source corresponding to the next scanning line regardless of the same light source. If the transport cycle of the inspected object 1 is matched with the time for imaging the inspected object 1, the inspected object 1 can be imaged as if more than one point were irradiated with light from one light source LD, and the number of light sources can be decreased.

The position of the inspected object 1 is detected by the photoelectric sensor 40 to obtain the transport cycle.

9. Ninth Embodiment

Figure 23:
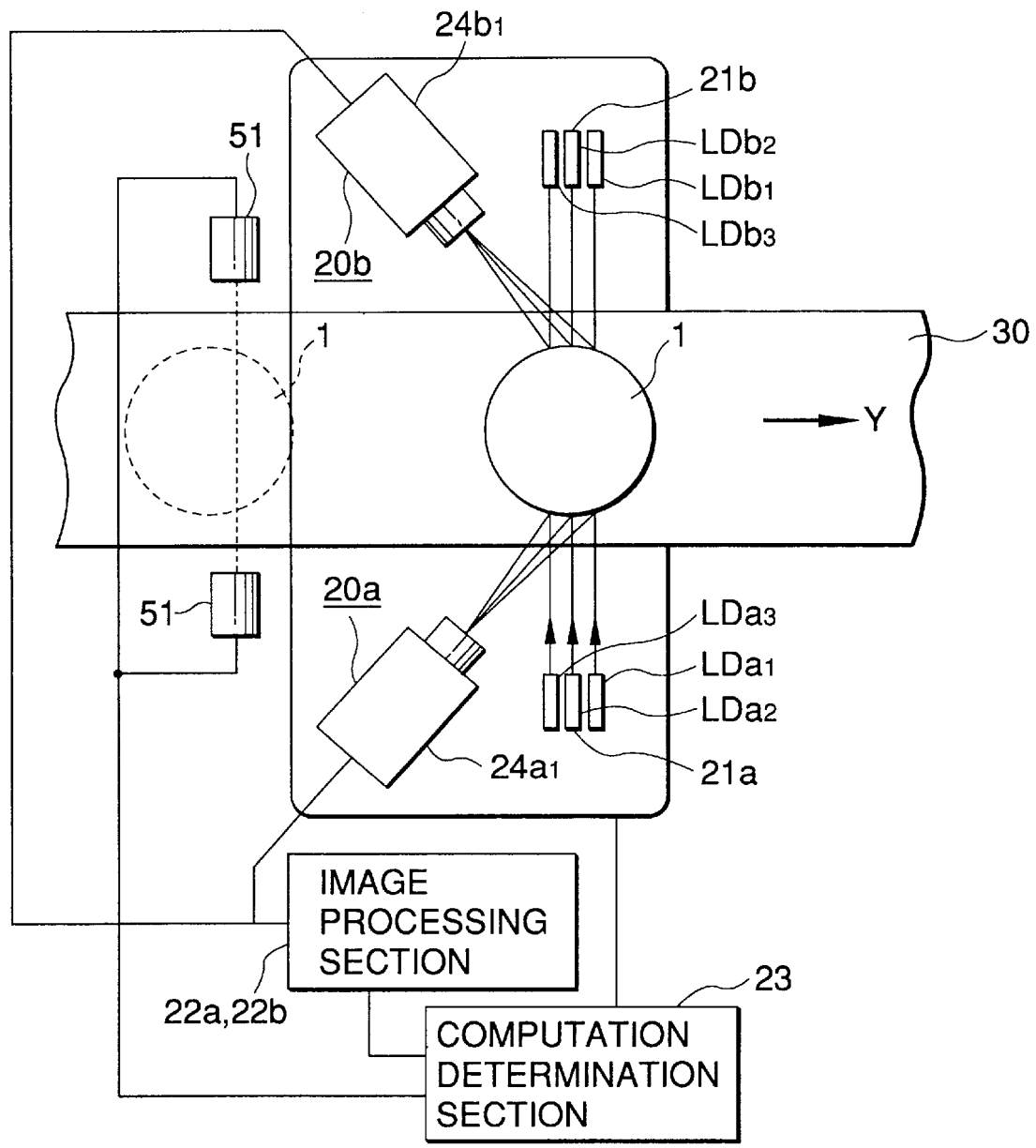
FIG. 23 is a plan layout drawing of the main part of the system of the ninth embodiment of the present invention.

Inspected objects 1 are transported on a transporter 30 at unequal transport intervals and in addition, often shift in the direction orthogonal to the transport direction. If the inspected object 1 is imaged in a state in which it shifts, slantwise incident slit light misses the inspected object 1 and the inspected object 1 cannot be detected. To cope with such an accident, in the embodiment, as shown in FIG. 22 and FIG. 23, a driving device 50 is provided for moving image pick-up devices $24a_1$ . . . and $24b_1$ . . . of image pick-up sections 20a and 20b and light sources 21a and 21b in the direction orthogonal to moving direction Y of the inspected object 1, and distance measurement sensors 51 are placed in the direction orthogonal to the moving direction Y in place of a photoelectric sensor. At the instant at which the inspected object 1 crosses the distance measurement sensors 51, a computation unit 23 finds a distance to the inspected object 1, further finds a shift amount from the distance, and controls the driving device 50 so as to correct the optical system position by the distance corresponding to the shift amount.

10. Tenth Embodiment

In the preceding embodiments, one image pick-up section is related to one inspection area of an inspected object 1. An object like a convex at the center like a cylindrical inspected object 1 may be unable to be detected on a plane pointing in the opposite direction to the image pick-up direction of an image pick-up section as a blind spot (blind spot zone). In such a case, if another image pick-up section is provided symmetrically with that image pick-up section with a light transmission axis between, the object can be imaged without the dead spot effect.

Figure 24:
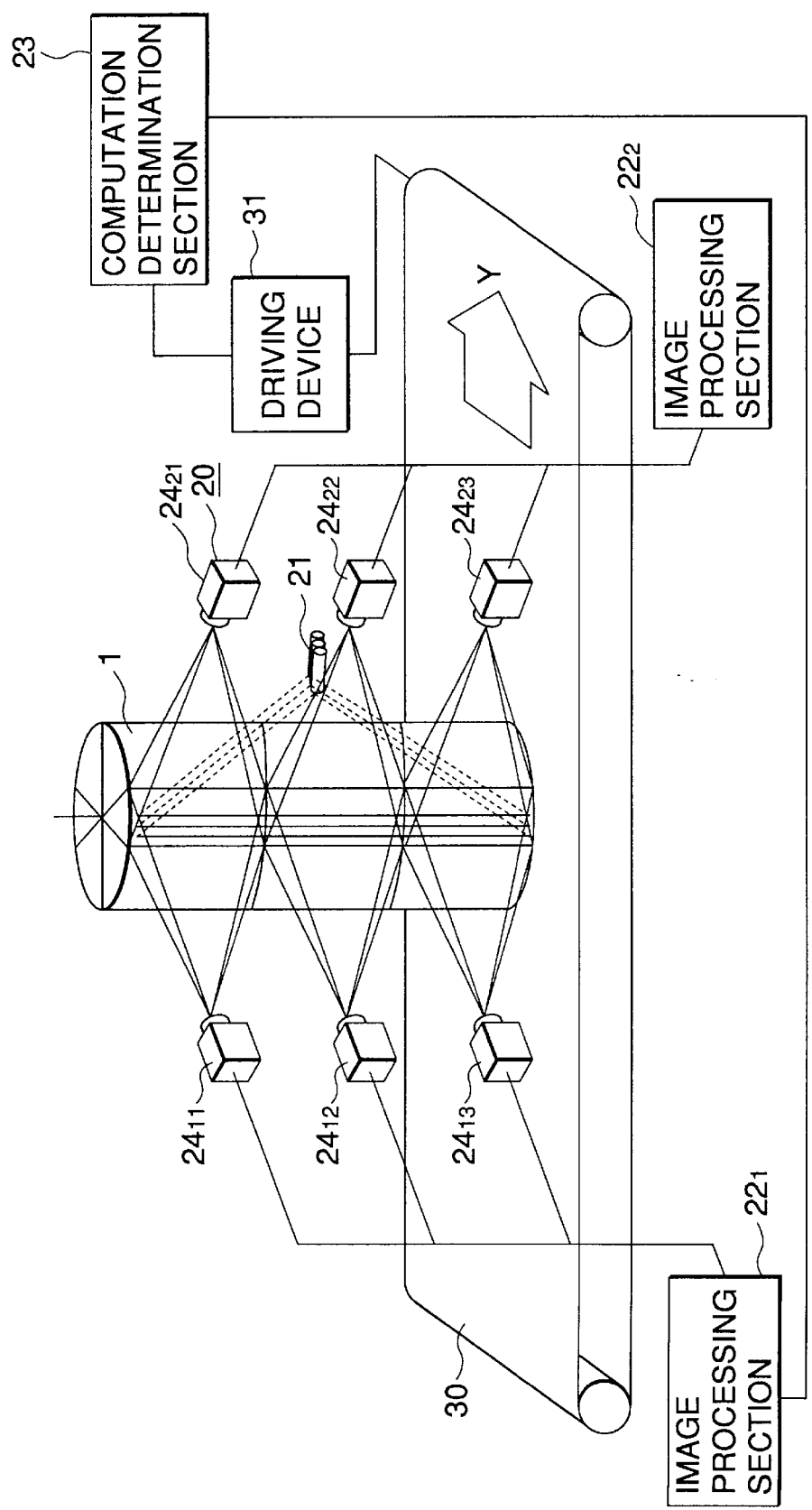
FIG. 24 is a perspective view of a system of a tenth embodiment of the present invention.
Figure 25:
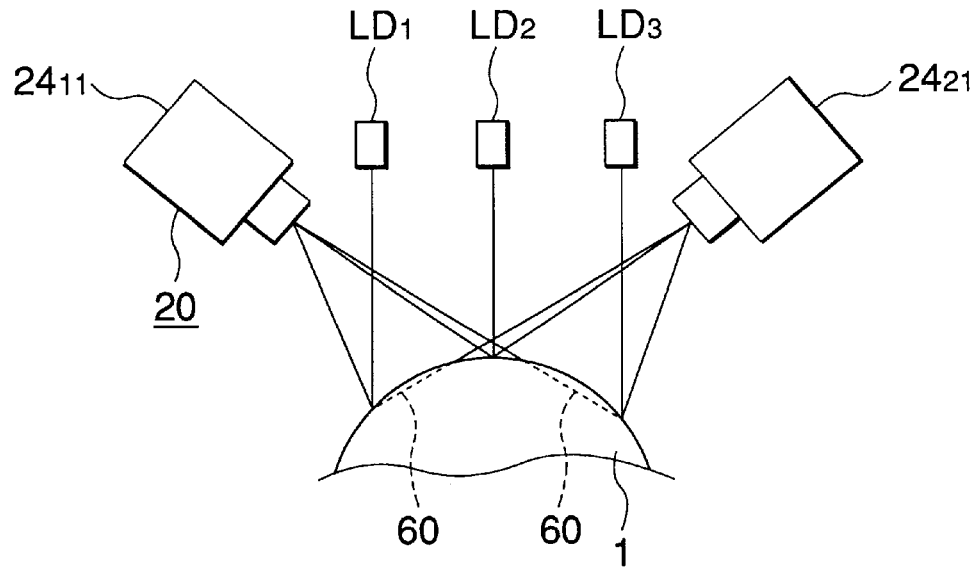
FIG. 25 is a schematic representation of the system of the tenth embodiment of the present invention.

Then, in a tenth embodiment of the present invention, as shown in FIG. 24 and FIG. 25, image pick-up devices $24_{11}$ . . . and different image pick-up devices $24_{21}$ . . . placed symmetrically with the image pick-up devices $24_{11}$ . . . make up an image pick-up section 20, image processing sections $22_1$ and $22_2$ are provided corresponding to image pick-up devices $24_{11}$ . . . and $24_{21}$ . . . , and a single light source group 21 is installed. Thus, according to the embodiment, the inspected object can be imaged without the effect of a blind spot zone 60.

The light source group 21 consists of light sources LD1 to LD3.

11. Eleventh Embodiment

Figure 26:
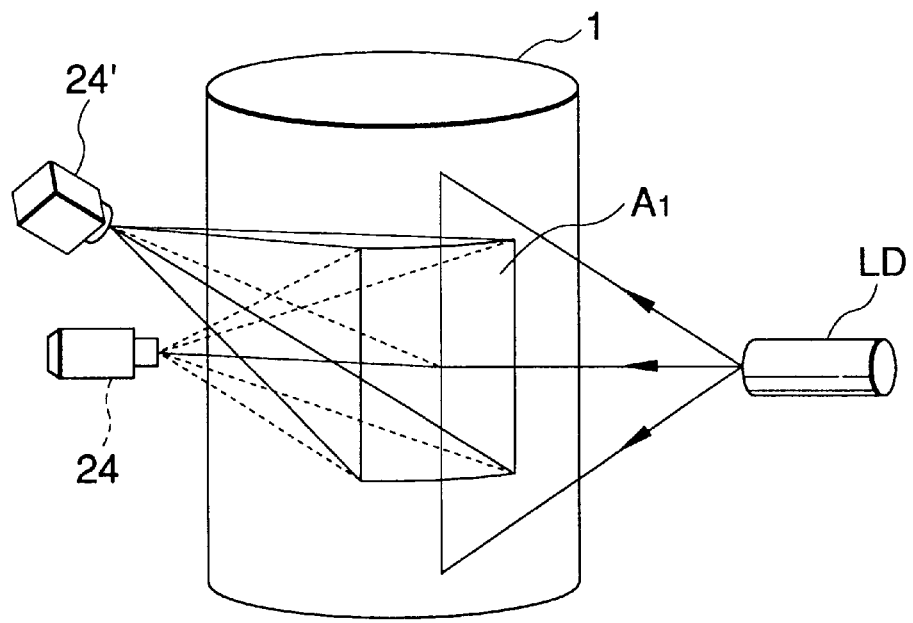
FIG. 26 is a schematic representation of a system of an eleventh embodiment of the present invention.

By the way, in the original positional relationship between an image pick-up section 20 in an image pick-up unit and a light source LD in a light source group 21, as shown in FIG. 26, on a plane defined by the sight line axis of an image pick-up device 24 and the light transmission axis of the light source LD for emitting slit light, the optical axis of the slit light is on the plane and crosses at right angles to the axis of an inspected object 1. However, if the inspected object 1 is a cylindrical object, scattered light in a cylindrical lens of the light source LD may become specular reflection light (stray light) and be incident on the image pick-up device 24 depending on the incidence angle of the slit light, causing a measurement error to occur. As countermeasures against it, the sight line axis of the image pick-up device 24 is made like 24' or the light transmission axis of the light source LD is inclined and scattered light is turned away from the sight line of the image pick-up device 24, whereby the error cause can be removed.

Figure 27:
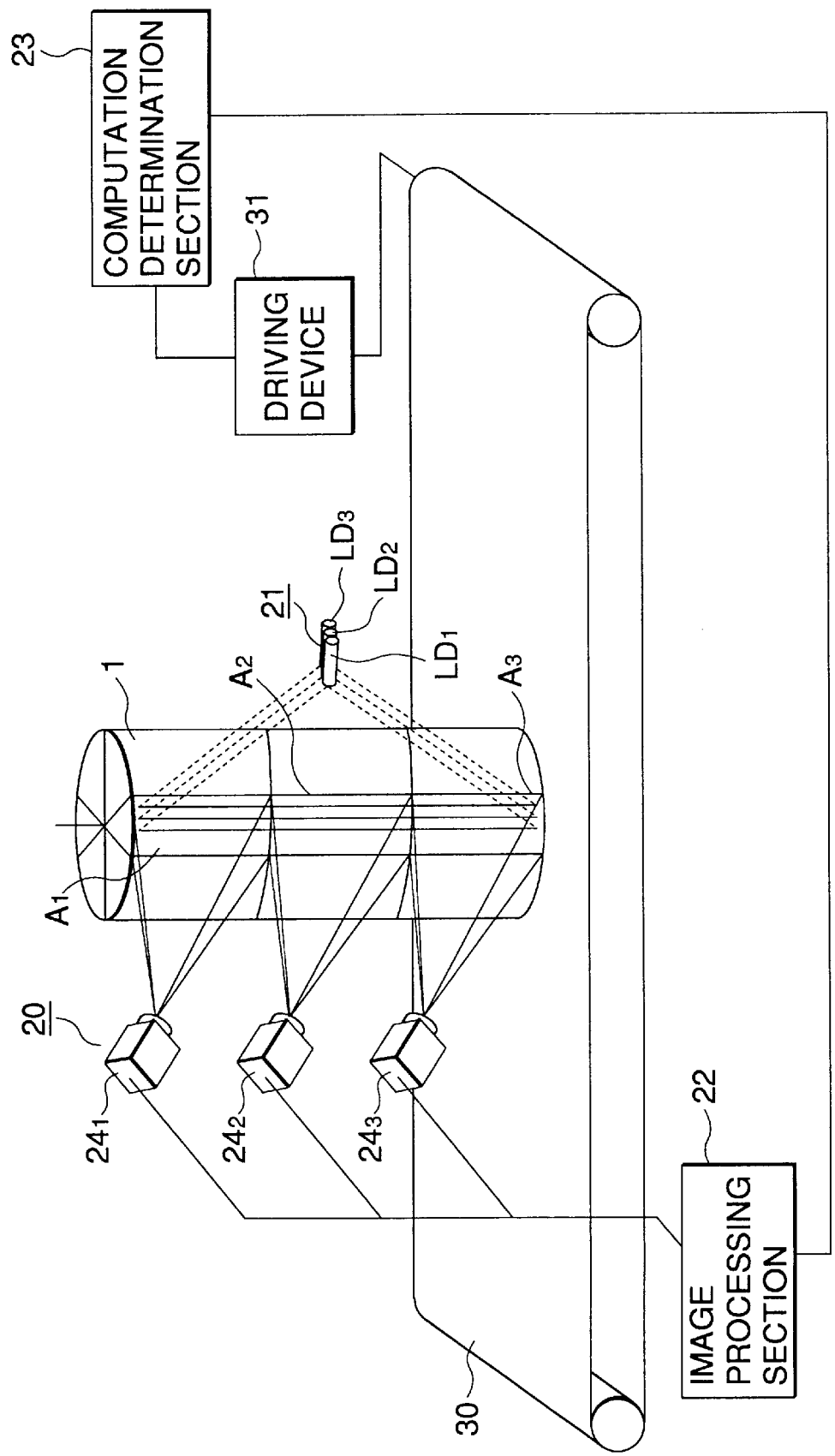
FIG. 27 is a perspective view of the system of the eleventh embodiment of the present invention.
Figure 28:
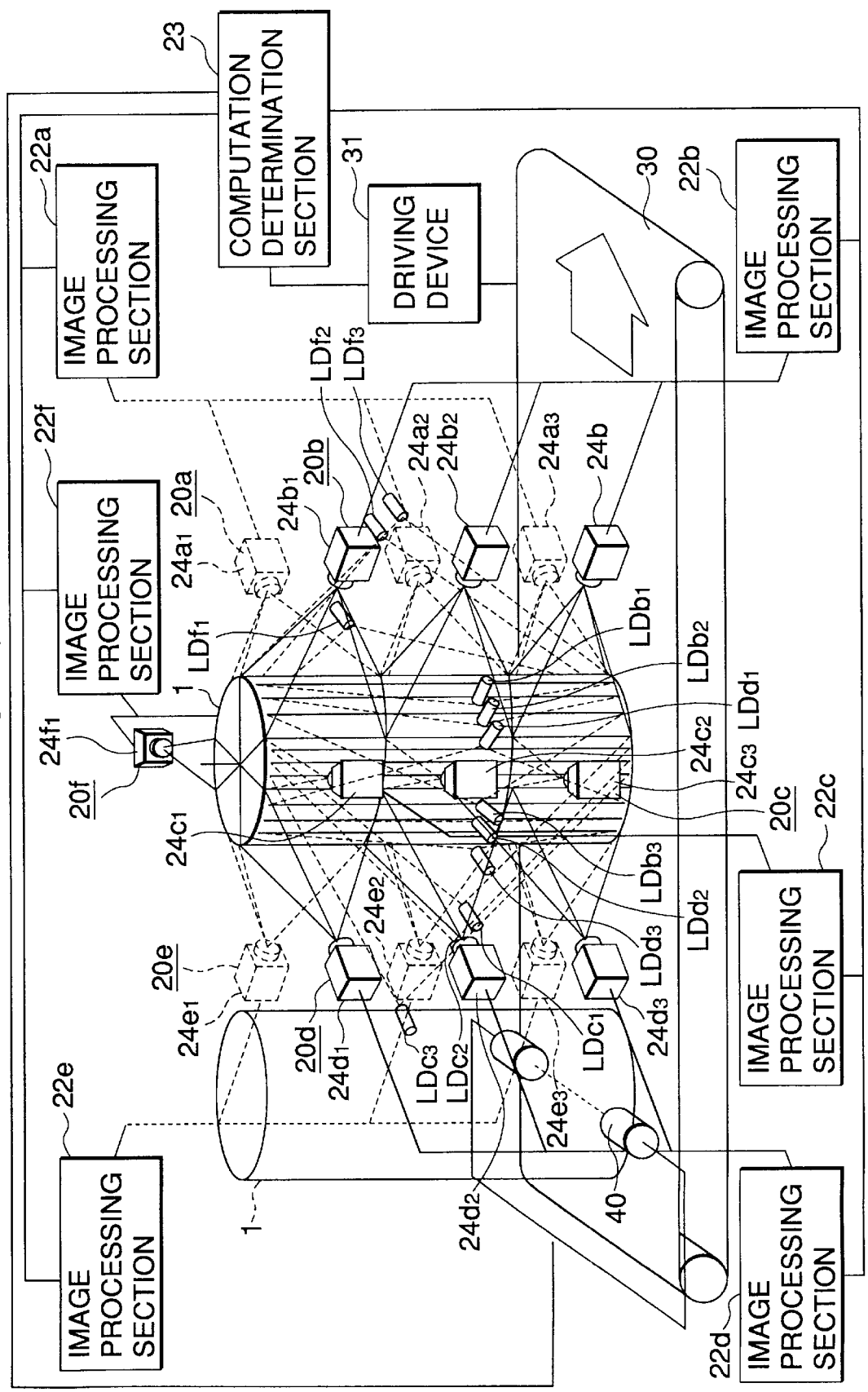
FIG. 28 is a perspective view of a system of a twelfth embodiment of the present invention.
Figure 29:
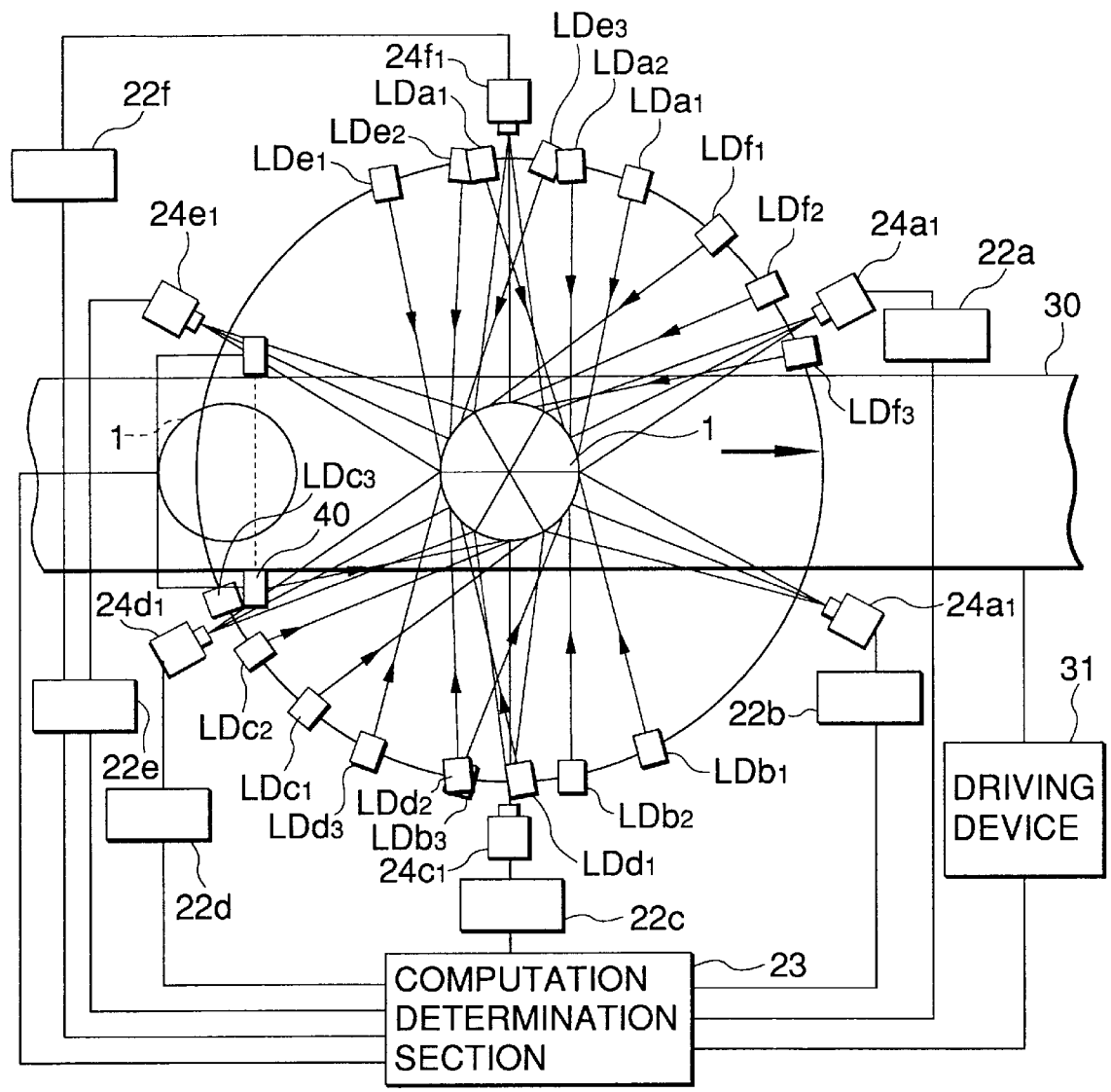
FIG. 29 is a plan layout drawing of the main part of the system of the twelfth embodiment of the present invention.

In the embodiment, as shown in FIG. 27, the sight line axes of the image pick-up devices $24_1$ . . . making up the image pick-up section 20 are inclined. Members identical with or similar to those previously described with reference to FIG. 8 are denoted by the same reference numerals in FIG. 27 and will not be discussed again.

If the sight line axes remain unchanged and the light transmission axes are inclined, a similar effect can be produced.

12. Twelfth Embodiment

In a twelfth embodiment of the present invention, light sources LDa1–LDa3 to LDf1–LDf3 of light source groups 21a to 21f corresponding to image pick-up sections 20a to 20f are not positioned on a transporter 30 and are placed so that the image pick-up sections 20a to 20f can image the full periphery of an inspected object 1 in batch.

According to the embodiment, the inspected object 1 can be inspected for surface form without being rotated by the transporter 30 and if the position of the inspected object 1 moving shifts, the light source groups or the image pick-up sections do not come in contact with the inspected object 1.

13. Thirteenth Embodiment

Figure 30:
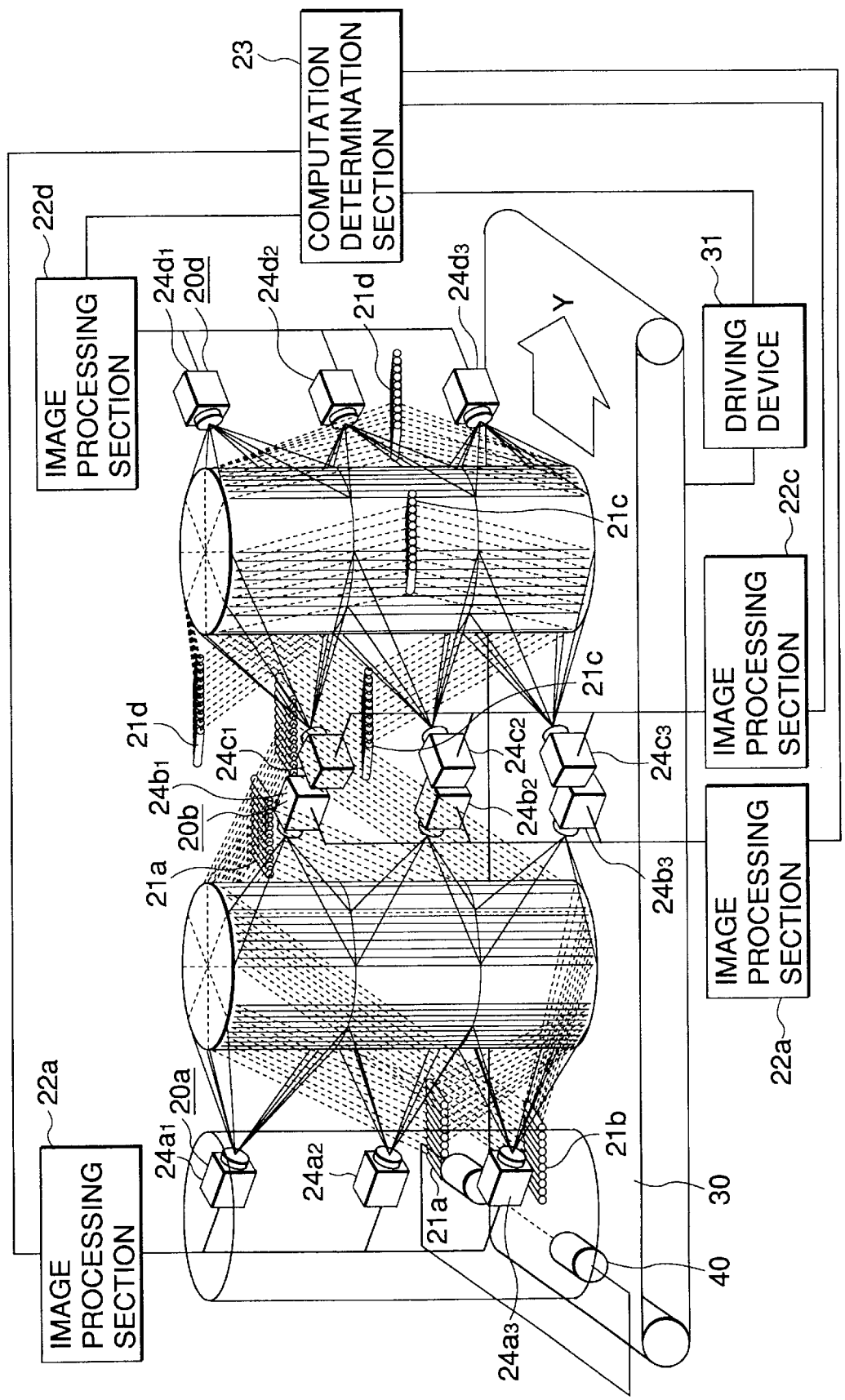
FIG. 30 is a perspective view of a system of a thirteenth embodiment of the present invention.

As shown in FIG. 30, a shading photoelectric sensor 40 is installed upstream a predetermined distance from the first image pick-up position in addition to the configuration of the fourth embodiment shown in FIG. 10, and the image pick-up timing at each image pick-up position is set with a time delay from the instant at which an inspected object 1 crosses a light beam of the photoelectric sensor 40. Therefore, if the transport pitches of the inspected objects 1 are discontinuous, the inspected objects 1 can always be imaged at the same image pick-up position. Members identical with those previously described with reference to FIG. 10 are denoted by the same reference numerals in FIG. 30 and will not be discussed again.

Since the number of slit light rays is greater than the object width, if the inspected object 1 shifts in the direction orthogonal to moving direction Y of the inspected object 1 and is transported, the effect is small.

As has been described heretofore, according to the present invention, the defect on the inspected object can be detected at high speed with high accuracy.

It is contemplated that numerous modifications may be made to the system of the present invention without departing from the spirit and scope of the invention as defined in the following claims.

What is claimed is:

1. A detecting system for a surface form of an object comprising:

a light source section emitting a plurality of slit-like probe rays incidenting on a predetermined inspected area of an inspected object at predetermined pitches;

an image pick-up section imaging reflected lights of the probe rays from the inspected area, the image pick-up section imaging the reflected lights from a direction different from a transmission axis of the light source section; and a computation section converting image data from the image pick-up section into data of surface height of the inspected object using a trigonometrical survey method.

2. A detecting system for a surface form of an object comprising:

at least one light source section emitting a plurality of slit-like probe rays incidenting on a predetermined inspected area of a cylindrical inspected object at predetermined pitches;

at least one image pick-up section imaging reflected lights of the probe rays from the corresponding inspected area, each image pick-up section detecting the reflected lights from a direction different from a transmission axis of the corresponding light source section; and a computation section converting image data from the image pick-up sections into data of surface height of the inspected object using a trigonometrical survey method, wherein a total inspected area defined by the light source section and the image pick-up section covers a full periphery of surface of the cylindrical inspected object.

3. The detecting system for the surface form of the object as set forth in claim 1, wherein each of the probe rays incidents at a same angle with tangents at incidence points on the inspected object.

4. The detecting system for the surface form of the object as set forth in claim 2, wherein each of the probe rays incidents at a same angle with tangents at incidence points on the inspected object.

5. The detecting system for the surface form of the object as set forth in claim 3 further comprising:

a transporter transporting the inspected object a to predetermined inspection position.

6. The detecting system for the surface form of the object as set forth in claim 3, wherein the image pick-up section includes a plurality of image pick-up devices disposed at equal pitches in a vertical direction, each of the image pick-up devices images respective inspected area defined so as to equally divide an entire inspected surface of the inspected object.

7. The detecting system for the surface form of the object as set forth in claim 3, wherein the light source section includes a light source and a light divergence member providing the plurality of slit probe rays from the light source.

8. The detecting system for the surface form of the object as set forth in claim 3, wherein the image pick-up section includes a plurality of image pick-up devices disposed so that a blind spot does not occur in the inspected area.

9. The detecting system for the surface form of the object as set forth in claim 3, wherein the slit probe rays does not cross at right angle to a plane defined by a transmission axis of the light source section and a sight line axis of the image pick-up section.

10. The detecting system for the surface form of the object as set forth in claim 4, further comprising:

a first inspection position where a half periphery of the surface of the inspected object is inspected;

a second inspection position where the other half periphery of the surface of the inspected object is inspected; and a transporter transporting the inspected object to the first inspection position, and transporting the inspected object to the second inspection position after a first image pick-up is finished.

11. The detecting system for the surface form of the object as set forth in claim 4, wherein the image pick-up section includes a plurality of image pick-up devices disposed at equal pitches in a vertical direction, each of the image pick-up devices images respective inspected area defined so as to equally divide an entire inspected surface of the inspected object.

12. The detecting system for the surface form of the object as set forth in claim 4, wherein the light source section includes a light source and a light divergence member providing the plurality of slit probe rays from the light source.

13. The detecting system for the surface form of the object as set forth in claim 4, wherein the image pick-up section includes a plurality of image pick-up devices disposed so that a blind spot does not occur in the inspected area.

14. The detecting system for the surface form of the object as set forth in claim 4, wherein the slit probe rays does not cross at right angle to a plane defined by a transmission axis of the light source section and a sight line axis of the image pick-up section.

15. The detecting system for the surface form of the object as set forth in claim 10, wherein the transporter further includes a rotation mechanism rotating the cylindrical inspected object at a predetermined angle after a first image pick-up to set another inspected area for a second image pick-up.

16. The detecting system for the surface form of the object as set forth in claim 5 further comprising:

a passing detection sensor provided upstream of an inspection position for detecting a passing of the inspected object, wherein the image pick-up is started after a predetermined period from the passing detection of the inspected object.

17. The detecting system for the surface form of the object as set forth in claim 5, wherein the slit light rays are numbered to compensate for a position shift in a direction orthogonal to transport direction of the inspected object.

18. The detecting system for the surface form of the object as set forth in claim 5, wherein the light source section includes a single light source emitting intermittently a single probe ray at a predetermined time interval corresponding to a time period in which the inspected object moves a distance of the predetermined pitch, the single light source emits the intermittent probe ray within a time from image pick-up start to end.

19. The detecting system for the surface form of the object as set forth in claim 5, wherein the light source section and the image pick-up section are disposed so as not to contact the moving inspected object during the image pick-up.

20. The detecting system for the surface form of the object as set forth in claim 5 further comprising:

a distance measuring sensor detecting a position shift amount of the inspected object in a direction orthogonal to the transport direction of the inspected object;

a correction member correcting positions of the light source section and the image pick-up position based on position shift data from the distance measuring sensor.

21. The detecting system for the surface form of the object as set forth in claim 10 further comprising:

a passing detection sensor provided upstream of the inspection position for detecting a passing of the inspected object, wherein the image pick-up is started after a predetermined period from the passing detection of the inspected object.

22. The detecting system for the surface form of the object as set forth in claim 10, wherein the slit light rays are numbered to compensate for a position shift in a direction orthogonal to a transport direction of the inspected object.

23. The detecting system for the surface form of the object as set forth claim 10, wherein the light source section includes a single light source emitting intermittently a single probe ray at a predetermined time interval corresponding to a time period in which the inspected object moves a distance of the predetermined pitch, the single light source emits the intermittent probe ray within a time from image pick-up start to end.

24. The detecting system for the surface form of the object as set forth in claim 10, wherein the light source section and the image pick-up section are disposed so as not to contact the moving inspected object during the image pick-up.

25. The detecting system for the surface form of the object as set forth in claim 10 further comprising:

a distance measuring sensor detecting a position shift amount of the inspected object in a direction orthogonal to the transport direction of the inspected object;

a correction member correcting positions of the light source section and the image pick-up position based on position shift data from the distance measuring sensor.

* * * * *